US012722009B2

(12) United States Patent
Grimes et al.

(10) Patent No.: US 12,722,009 B2
(45) Date of Patent: Sep. 1, 2026

(54) CURRENT STIMULATION UTILIZING ACTIVE CHARGE BALANCE PHASE

(71) Applicant: BIOTRONIK SE & Co. KG, Berlin (DE)

(72) Inventors: John Grimes, Tualatin, OR (US); Vighnesh Rudra Das, Katy, TX (US); Marcelo Baru, Tualatin, OR (US); Brad McMillan, Lake Oswego, OR (US); Linh Thuy Nguyen, Missouri City, TX (US); Richard Yi Chen Tseng, Portland, OR (US); David Genzer, Bay City, TX (US); Ashok Nedungadi, Lake Oswego, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 282 days.

(21) Appl. No.: 18/285,068

(22) PCT Filed: Mar. 14, 2022

(86) PCT No.: PCT/EP2022/056433
§ 371 (c)(1),
(2) Date: Sep. 29, 2023

(87) PCT Pub. No.: WO2022/207285
PCT Pub. Date: Oct. 6, 2022

(65) Prior Publication Data

US 2024/0181257 A1 Jun. 6, 2024

Related U.S. Application Data

(60) Provisional application No. 63/168,607, filed on Mar. 31, 2021.

(30) Foreign Application Priority Data

Apr. 29, 2021 (EP) .................................... 21171291

(51) Int. Cl.
*A61N 1/36* (2006.01)

(52) U.S. Cl.
CPC ..... *A61N 1/36062* (2017.08); *A61N 1/36125* (2013.01); *A61N 1/36153* (2013.01)

(58) Field of Classification Search
CPC ........... A61N 1/36062; A61N 1/36125; A61N 1/36153; A61N 1/3615; A61N 1/3603; A61N 1/36142; A61N 1/0551
See application file for complete search history.

(56) References Cited

U.S. PATENT DOCUMENTS

| | | | | |
|---|---|---|---|---|
| 2011/0160809 A1* | 6/2011 | Cox | H02J 7/00711 607/63 |
| 2014/0336729 A1* | 11/2014 | Franke | A61N 1/36125 607/63 |

(Continued)

FOREIGN PATENT DOCUMENTS

| | | | |
|---|---|---|---|
| WO | WO 2014/134075 A1 | 9/2014 | |
| WO | WO-2020097500 A2 * | 5/2020 | A61N 1/37211 |

OTHER PUBLICATIONS

International Search Report and Written Opinion for PCT/EP2022/056433 mailed May 23, 2022, 18 pages.

*Primary Examiner* — Niketa Patel
*Assistant Examiner* — Joshua Brendon Solomon
(74) *Attorney, Agent, or Firm* — FBT Gibbons LLP

(57) ABSTRACT

A medical device provides electrical stimulation. The medical device includes electric circuitry configured to perform active charge compensation. The electric circuitry is connectable to at least one electrode arrangement for electrical stimulation. The electric circuitry includes monitoring means configured to monitor at least one voltage associated with a stimulation network; at least one variable resistive element configured to provide a voltage drop used in the active charge compensation; and adjustment means config- (Continued)

ured to dynamically adjust a resistance value of the at least one variable resistive element during the active charge compensation based on the at least one monitored voltage. The adjustment means is a finite state machine for neuro-stimulation.

20 Claims, 16 Drawing Sheets

(56) References Cited

U.S. PATENT DOCUMENTS

| | | | | |
|---|---|---|---|---|
| 2019/0255333 | A1 | 8/2019 | Baru et al. | |
| 2019/0374776 | A1* | 12/2019 | Mishra | A61N 1/3752 |
| 2020/0155851 | A1 | 5/2020 | Boor et al. | |
| 2021/0386994 | A1* | 12/2021 | Scanlan | A61N 1/326 |

* cited by examiner 200
202
Ohmic Adjustment Control
Auto_Adjustment Control
Ohmic Adjustment Control Signals
ADJ_CMP_P_out
ADJ_CMP_N_out
Therapy Select
RDAC register
RDAC_CTRL[7:0]
VISTIM
204_0
204_N
214
$V_{THR\_P}$
ADJ_CMP_P_out
ADJ_CMP_N_out
212
$V_{THR\_N}$
VISTIM
VSS
RDAC_IN_P
SW_RDAC_P
SW_RDAC_n
RDAC_IN_N
RDAC_P
RDAC_CTRL[7:0]
208
To all DRIVER MODULES
RDAC_n
RDAC_CTRL[7:0]
206
To all DRIVER MODULES
VSS
210_N
102_N
Blocking Cap
Blocking Cap
210_0
102_0

Excursion during Active Balance phase due to Voltage Stacking
$V_{THR\_P}$
STIM_EN
BAL_EN
DRV_PAD
AUTO_ADJ_CMP_STRB
ADJ_CMP_OUT
RDAC_CTRL
Adjustment
Optimization
Convergence

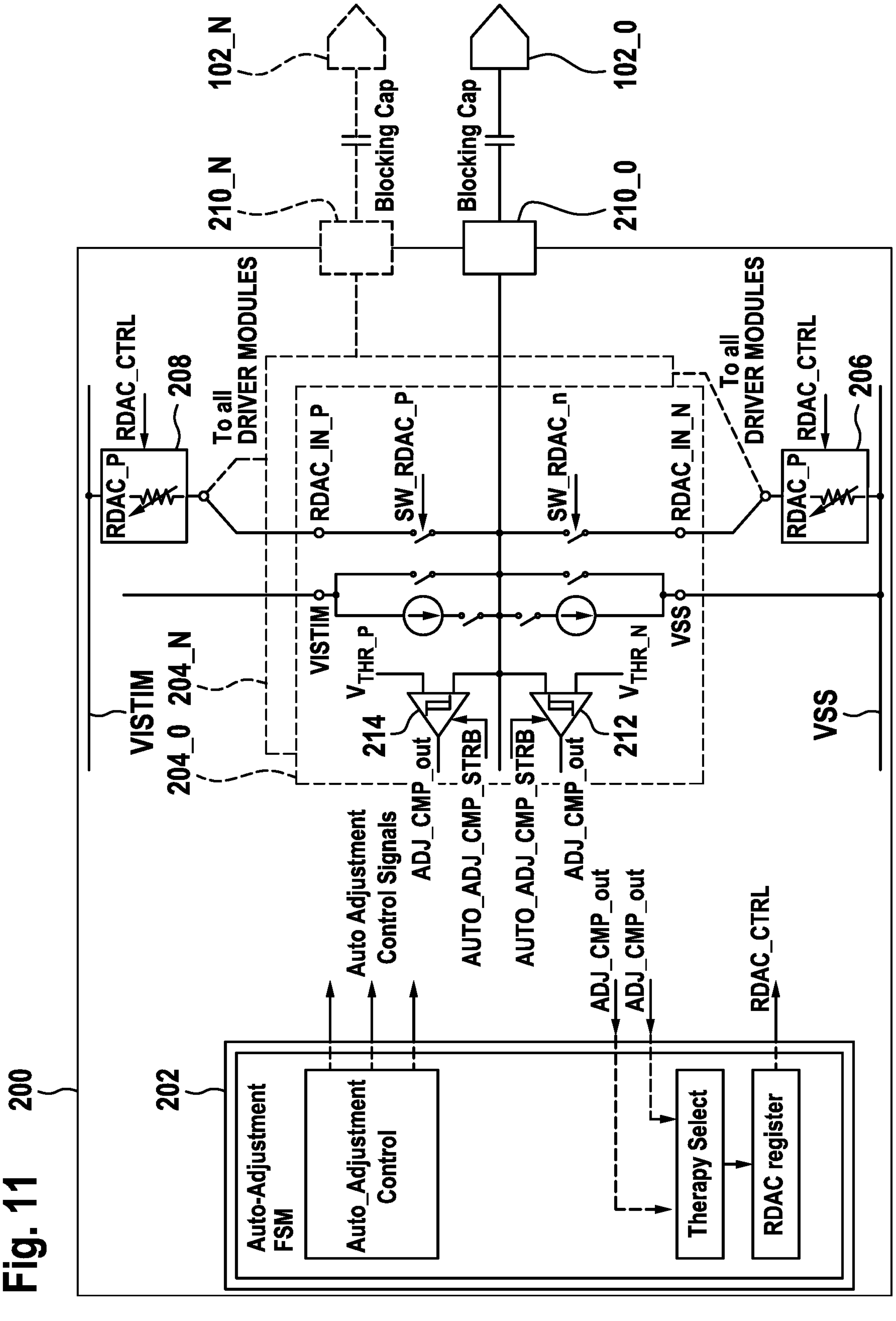

Fig. 11
200
202
Auto-Adjustment FSM
Auto_Adjustment Control
Therapy Select
RDAC register
Auto Adjustment Control Signals
ADJ_CMP_out
AUTO_ADJ_CMP_STRB
AUTO_ADJ_CMP_STRB
ADJ_CMP_out
ADJ_CMP_out
ADJ_CMP_out
RDAC_CTRL
204_0
204_N
VISTIM
214
212
$V_{THR\_P}$
$V_{THR\_N}$
VISTIM
VSS
VSS
RDAC_IN_P
SW_RDAC_P
SW_RDAC_n
RDAC_IN_N
RDAC_P
208
RDAC_CTRL
To all DRIVER MODULES
RDAC_P
206
RDAC_CTRL
To all DRIVER MODULES
210_N
210_0
Blocking Cap
Blocking Cap
102_N
102_0

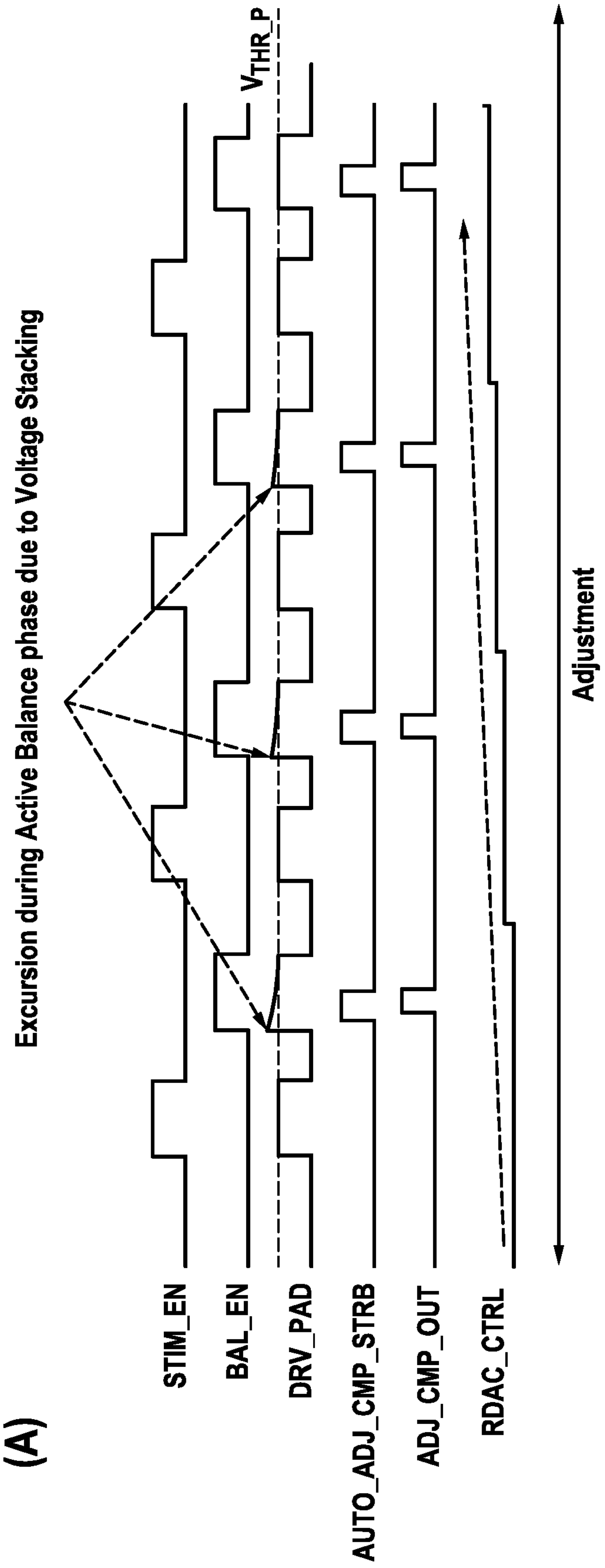
Fig. 12 part 1
(A)
Excursion during Active Balance phase due to Voltage Stacking
$V_{THR\_P}$
STIM_EN
BAL_EN
DRV_PAD
AUTO_ADJ_CMP_STRB
ADJ_CMP_OUT
RDAC_CTRL
Adjustment

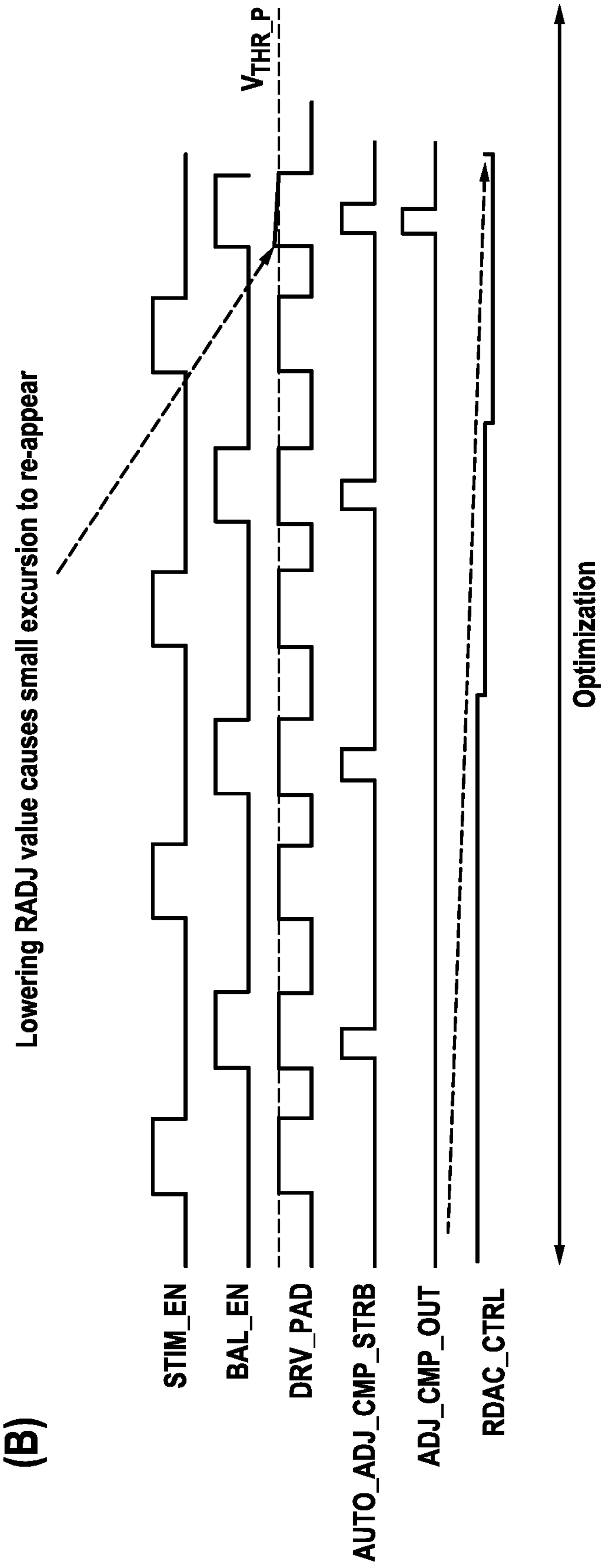
Fig. 12 part 2
(B)
Lowering RADJ value causes small excursion to re-appear
$V_{THR\_P}$
STIM_EN
BAL_EN
DRV_PAD
AUTO_ADJ_CMP_STRB
ADJ_CMP_OUT
RDAC_CTRL
Optimization Fig. 12 part 3
(C)
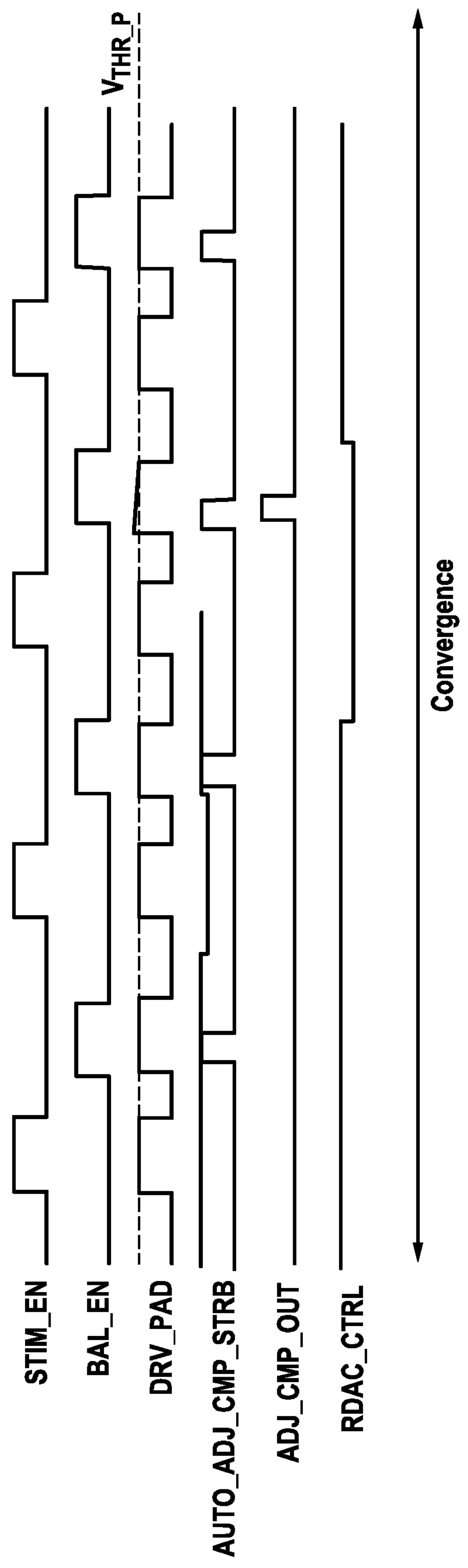

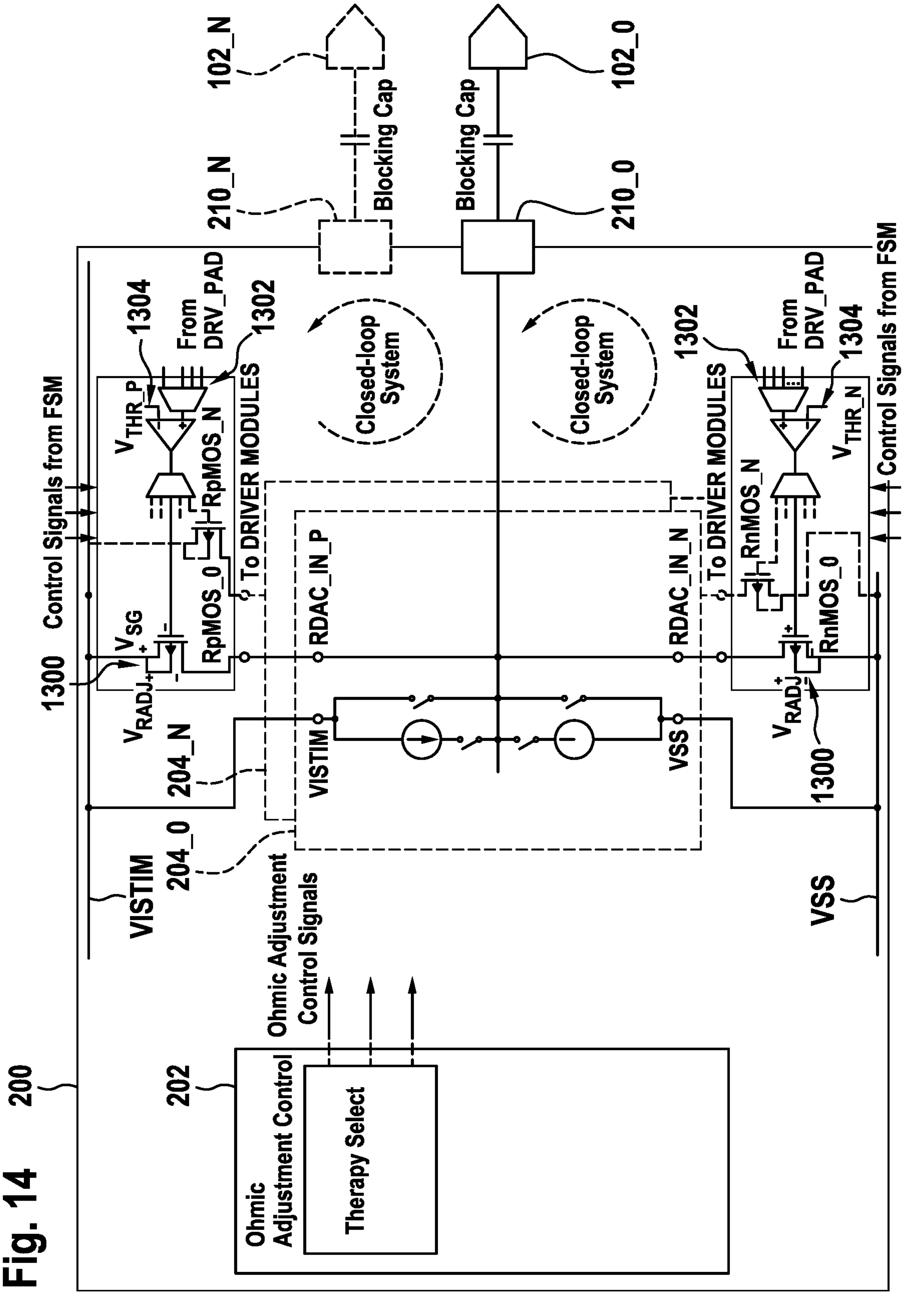

Fig. 14
200
1300
Control Signals from FSM
VISTIM
202
204_0
204_N
$V_{RADJ}$
$V_{SG}$
$V_{THR\_P}$
1304
From DRV_PAD
RpMOS_0
RpMOS_N
To DRIVER MODULES
1302
210_N
102_N
Ohmic Adjustment Control
Therapy Select
Ohmic Adjustment Control Signals
VISTIM
RDAC_IN_P
Closed-loop System
Blocking Cap
Blocking Cap
Closed-loop System
210_0
102_0
VSS
RDAC_IN_N
To DRIVER MODULES
1302
RnMOS_N
$V_{RADJ}$
From DRV_PAD
VSS
1300
RnMOS_0
$V_{THR\_N}$
1304
Control Signals from FSM

CURRENT STIMULATION UTILIZING ACTIVE CHARGE BALANCE PHASE

Embodiments of the present disclosure relate to a medical device and a method for electrical stimulation, in particular electrical neurostimulation. Embodiments of the present disclosure relate more particularly to a real-time adjustment for active charge-balanced current stimulation.

For electrical neurostimulation, providing safe therapy and achieving charge neutrality are of utmost importance. Neurostimulation is delivered using an implantable pulse generator and bio-compatible electrodes, which interface with the human body tissue. This electrode-tissue interface can be modeled as an electrical network comprising of passive elements such as resistors and capacitors. A typical current-based neurostimulation network comprises of current drivers, bio-compatible electrodes, DC blocking capacitors (for safety) and human body tissue.

To ensure charge neutrality of the therapy, e.g. a traditional pulse-based therapy, stimulation is accompanied with a charge balance phase. The charge balance phase essentially reverses the chemical reactions triggered by the stimulation charge, after a stipulated time duration known as interphase delay, based on the therapy efficacy requirements, to bring the electrode potential back to its pre-pulsing value. Depending on the frequency of the therapy, either passive charge balancing or active charge balancing is employed. Unlike passive charge balancing which depends on the electrode-tissue impedance to return the electrode potential back to neutral, active charge balancing uses active circuit elements to quickly revert the stimulation charge injected, thus enabling therapies needing higher stimulation frequency.

During the stimulation phase, when current flows through the stimulation network, charges build-up across the capacitive elements that appear as voltage with defined polarity, known as voltage stacking. In the subsequent active charge balance phase, current of equal or fractional magnitude as the stimulation duration will flow in the opposite direction. If the active balance current magnitude is equal to the stimulation current magnitude, the current durations will be equal, and for fractional magnitudes, the duration will be multiplied. This current reversal in combination with the reversed polarity voltage stacking at the DC blocking capacitors and electrode-tissue capacitances can cause the neurostimulation application specific integrated circuit (ASIC) pads of the implantable pulse generator to have excursions above therapy supply rail or below system ground, in the initial period of the active balance phase. Such excursions can activate parasitic diodes or protection structures, leading to uncontrolled unbalanced stimulation which may cause hazardous electrode potentials resulting in electrode corrosion. Further, current injection into the ASIC substrate may impact its performance.

In light of the above, a medical device and a method for electrical stimulation are provided that overcomes at least some of the problems in the art.

It is an object of the present disclosure to provide a medical device and method for handling accumulated voltages in a neurostimulation electrical network. It is another object of the present disclosure to make electrical neurostimulation therapy more power efficient.

The objects are solved by the features of the independent claims. Preferred embodiments are defined in the dependent claims.

According to an independent aspect of the present disclosure, a medical device for electrical stimulation, in particular electrical neurostimulation such as spinal cord stimulation (SCS), is provided.

The medical device may be a pulse generator, preferably an implantable pulse generator (IPG), comprising a programmable application specific integrated circuit (ASIC) device.

The medical device preferably includes electric circuitry configured to perform active charge compensation, said electric circuitry being connectable to at least one electrode arrangement for electrical stimulation. The electric circuitry includes monitoring means configured to monitor at least one voltage associated with a stimulation network; at least one variable resistive element configured to provide a voltage drop, or ohmic voltage drop, used in the active charge compensation; and adjustment means configured to dynamically adjust a resistance value of the at least one variable resistive element during the active charge compensation based on the at least one monitored voltage. The resistive element can also be called resistor. Furthermore, the resistance value can also be called resistance parameter, and the charge compensation can also be called charge balancing.

The at least one electrode arrangement may include at least one neurostimulation electrode, such as one or more percutaneous leads. The at least one electrode arrangement may be implantable in a human body, e.g. for spinal cord stimulation (SCS).

According to some embodiments, which can be combined with other embodiments described herein, the at least one variable resistive element is connected in series with an active charge compensation path or an active charge balance compensation path. For example, the charge compensation path may be defined between a system voltage required for the stimulation phase (namely VISTIM) and a system ground (namely VSS).

According to some embodiments, which can be combined with other embodiments described herein, the electric circuitry includes at least one circuitry pad connectable to the at least one electrode arrangement. The at least one circuitry pad may include, or be, at least one integrated circuit (ASIC) pad, such as at least one neurostimulation application specific integrated circuit (ASIC) pad.

Preferably, the voltage monitored by the monitoring means is a voltage or potential at (or of) the at least one circuitry pad.

According to some embodiments, which can be combined with other embodiments described herein, each electrode arrangement includes a stimulation electrode and a return electrode. The stimulation electrode may deliver cathodic stimulation to tissue e.g. using a current sink element to a system ground (e.g. VSS). The return electrode may complete the electrical path by connecting tissue to a system voltage (e.g. a supply rail, such as VISTIM).

Preferably, the at least one circuitry pad includes a stimulation pad connectable or connected to the stimulation electrode and a return pad connectable to the return electrode.

According to some embodiments, which can be combined with other embodiments described herein, the at least one variable resistive element includes a first variable resistive element connected between a system ground (e.g. VSS) and the return pad. In particular, the return pad, the first variable resistive element and the system ground may be connected in series.

Preferably, the monitoring means is configured to monitor a stimulation voltage at the stimulation pad and provide a result of the monitoring to the adjustment means. The stimulation pad and/or the return pad can be, added by or replaced by any other bio-electrically coupled non-participating pads.

Preferably, the adjustment means is configured to adjust the first variable resistive element (i.e. a resistance value thereof) based on the monitored stimulation voltage. For example, the adjustment means can adjust the first variable resistive element to keep a voltage at the stimulation pad above the system ground. Thereby, excursions below the system ground can be prevented.

According to some embodiments, which can be combined with other embodiments described herein, the at least one variable resistive element includes a second variable resistive element connected between the system voltage required for the stimulation phase and the stimulation pad. In particular, the stimulation pad, the second variable resistive element and the system voltage may be connected in series.

Preferably, the monitoring means is configured to monitor a return voltage at the return pad and provide a result of the monitoring to the adjustment means.

Preferably, the adjustment means is configured to adjust the second variable resistive element based on the monitored return voltage. For example, the adjustment means can adjust the second variable resistive element to keep the voltage at the return pad below the system voltage. Thereby, excursions above the system voltage or supply rail can be prevented.

According to some embodiments, which can be combined with other embodiments described herein, the monitoring means includes at least one comparator configured to compare the monitored voltage to at least one threshold.

Preferably, the at least one comparator is configured to output a result of the comparison to the adjustment means.

Preferably, the at least one comparator includes a first comparator configured to compare the stimulation pad voltage to a first threshold. The first comparator may be configured to output a result of the comparison to the adjustment means. The adjustment means may then adjust the first variable resistive element based on the comparison between the stimulation pad voltage and the first threshold.

Additionally, or alternatively, the at least one comparator may include a second comparator configured to compare the return pad voltage to a second threshold. The second comparator may be configured to output a result of the comparison to the adjustment means. The adjustment means may then adjust the second variable resistive element based on the comparison between the return pad voltage and the second threshold.

According to some embodiments, which can be combined with other embodiments described herein, the adjustment means is a finite state machine for neurostimulation. A finite state machine is a mathematical model of computation. It is an abstract machine that can be in exactly one of a finite number of states at any given time. The finite state machine may receive an input from the monitoring means, such as the at least one comparator, and output control signals to control the at least one variable resistive element.

According to some embodiments, which can be combined with other embodiments described herein, the at least one variable resistive element is a DAC (digital-analog-converter), in particular a MOSFET (metal oxide semiconductor field-effect transistor) DAC.

The DAC can provide a digitally assisted real-time feedback-based adjustment scheme, in particular a sampled-time digitally assisted real-time feedback-based adjustment scheme. For example, a comparator-based monitoring of all the ASIC pads combined with an adjustable resistor DAC/MOSFET DAC can provide closed-loop, real-time adjustment of the stimulation network impedance.

Thus, the at least one variable resistive element can be a DAC, in particular a MOSFET DAC.

According to some embodiments, which can be combined with other embodiments described herein, the at least one resistor is a MOSFET. A drain-to-source on resistance, RDSON, of the MOSFET may provide the (ohmic) voltage adjustment. The MOSFET RDSON can provide a continuous-time analog feedback-based adjustment by modulating the MOSFET RDSON, which enables a continuous adjustment of the stimulation network impedance.

According to some embodiments, which can be combined with other embodiments described herein, the medical device is an implantable pulse generator, preferably comprising a neurostimulation programmable application specific integrated circuit device.

According to another independent aspect of the present disclosure, a method for active charge compensation in neurostimulation is provided. The method includes monitoring a voltage associated with a stimulation network; and dynamically adjusting a resistance value of at least one variable resistive element during the active charge compensation based on the monitored voltage to provide an, preferably optimum, voltage drop (or ohmic voltage drop) used in the active charge compensation.

Embodiments are also directed at systems/devices for carrying out the disclosed methods and include system/device aspects for performing each described method aspect. These method aspects may be performed by way of hardware components, a computer programmed by appropriate software, by any combination of the two or in any other manner. Furthermore, embodiments according to the invention are also directed at methods for operating the described device/system. It includes method aspects for carrying out every function of the device/system.

According to another independent aspect of the present disclosure, a machine-readable medium is provided. The machine-readable medium includes instructions executable by one or more processors to implement the method for active charge compensation in neurostimulation of the embodiments of the present disclosure.

The (e.g. non-transitory) machine readable medium may include, for example, optical media such as CD-ROMs and digital video disks (DVDs), and semiconductor memory devices such as Electrically Programmable Read-Only Memory (EPROM), and Electrically Erasable Programmable Read-Only Memory (EEPROM). The machine-readable medium may be used to tangibly retain computer program instructions or code organized into one or more modules and written in any desired computer programming language. When executed by, for example, one or more processors such computer program code may implement one or more of the methods described herein.

So that the manner in which the above recited features of the present disclosure can be understood in detail, a more particular description of the disclosure, briefly summarized above, may be had by reference to embodiments. The accompanying drawings relate to embodiments of the disclosure and are described in the following:

FIG. 11 shows the ASIC and blocking capacitors of a medical device for electrical stimulation according to embodiments described herein;

FIG. 12 shows a timing diagram of a digitally assisted real-time ohmic adjustment scheme for different phases according to embodiments described herein;

FIG. 14 shows a continuous-time feedback based real-time ohmic adjustment scheme according to embodiments described herein.

Reference will now be made in detail to the various embodiments of the disclosure, one or more examples of which are illustrated in the figures. Within the following description of the drawings, the same reference numbers refer to same components. Generally, only the differences with respect to individual embodiments are described. Each example is provided by way of explanation of the disclosure and is not meant as a limitation of the disclosure. Further, features illustrated or described as part of one embodiment can be used on or in conjunction with other embodiments to yield yet a further embodiment. It is intended that the description includes such modifications and variations.

The current reversal used in active charge balancing can cause excursions above therapy supply rail or below system ground in the initial period of the active balance phase. Such excursions can activate parasitic diodes or protection structures, leading to uncontrolled unbalanced stimulation which may cause hazardous electrode potentials.

The present disclosure provides a real-time closed-loop system which dynamically adjusts a voltage drop (or ohmic voltage drop) used in the active charge balance compensation based on a voltage associated with the stimulation network. This system not only remedies the situation of voltages increasing beyond the power rails but also makes the therapy power-efficient, which is an important feature for implantable pulse generators requiring higher stimulation frequencies.

Further benefits of the present disclosure are apparent from the following description and the accompanying drawings.

Figure 1:
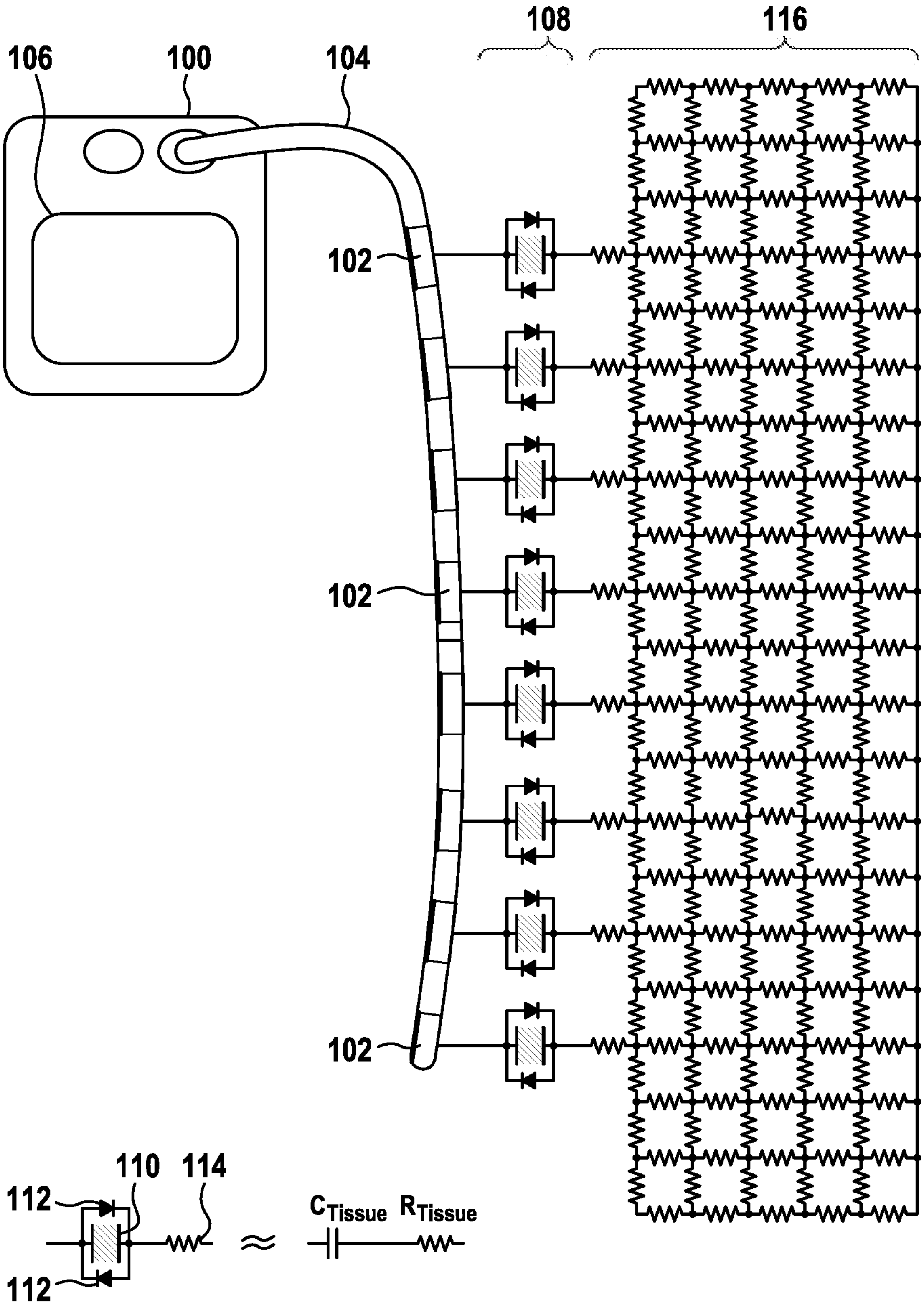
FIG. 1 shows a schematic view of a neurostimulation system/front-end with electrode-electrolyte interface and electrically modeled tissue.

FIG. 1 shows a schematic view of a neurostimulation system/front-end with electrode-electrolyte interface and electrically modeled tissue.

The neurostimulation system has an implantable pulse generator 100, electrodes 102 and a percutaneous lead 104 for neurostimulation, such as spinal cord stimulation (SCS). The electrodes 102 can also be called an electrode arrangement 102. Although only one percutaneous lead 104 and eight electrodes 102 are shown, and the embodiments are described for simplicity in terms of an SCS application, the present disclosure can be extended and applied to any electrical stimulation application, implantable or not, of any number of different leads 104 and electrodes 102. Alternatively, or additionally, a medical device 100 is shown, here the implantable pulse generator 100, comprising the percutaneous lead 104 and/or the electrodes 102 (also to be read on FIG. 1).

Neurostimulation is enabled by a highly programmable application specific integrated circuit (ASIC) 106 which can support a multitude of therapy options to cater to various patient needs. This ASIC 106 resides in medical device 100, here the implantable pulse generator 100 and is configured to drive the stimulation network including, or consisting of, the bio-compatible electrodes, DC blocking capacitors and human-body tissue as shown in FIG. 1. For the SCS example being described, the human-body tissue resistive nature is modeled as a 2D array of varying resistors 116 due to the rotational symmetry of the electrodes 102. The electrode-electrolyte (or electrode-tissue) interface 108 (Helmholtz layer) can be modeled to address two phenomena—the displacement current and reversible Faradaic reactions, as well as potential irreversible Faradaic reactions. The displacement current and reversible Faradaic reactions can be represented using a constant phase element (CPE) 110, whereas the irreversible Faradaic reactions can be represented using diodes 112. Following the electrode-electrolyte interface is the access resistance 114 that accounts for the resistance in the close vicinity of each electrode 102 in the electrolyte medium.

The Faradaic conduction is modeled using diodes 112 to capture the irreversible electro-chemical reactions that may occur at the electrode. Such reactions are not associated with steady-state therapy-delivery conditions, but they may be reached during therapy transients. CPE 110 is a double-layer capacitance, and the electrolyte here includes nervous tissue in the epidural space of the spinal cord.

For simplicity, the electrode-electrolyte interface 108 and human-body tissue 116 are electrically represented as a combination of tissue capacitors $C_{Tissue}$, and tissue resistor $R_{Tissue}$. The stimulation network can thus be formed by a network with the interface 108 and tissue 116.

Figure 2:
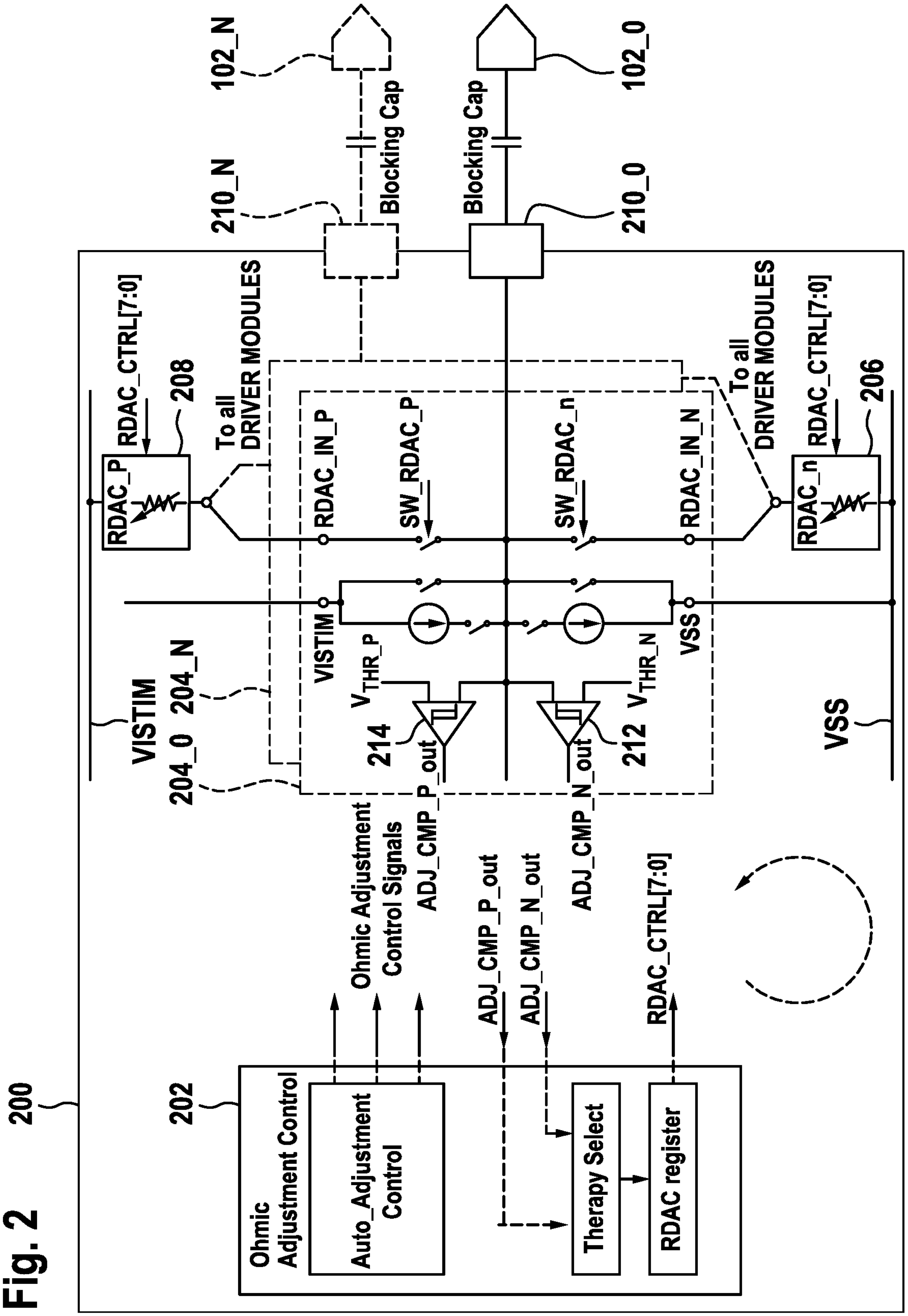
FIG. 2 shows the ASIC and blocking capacitors of a medical device for electrical stimulation according to embodiments described herein.

FIG. 2 shows a neurostimulation ASIC 200 for electrical stimulation according to embodiments described herein. The ASIC 200 can be the ASIC 106 in FIG. 1. The medical device of the present disclosure may be an implantable pulse generator, e.g. the implantable pulse generator 100 in FIG. 1, which includes the neurostimulation ASIC 200.

The neurostimulation ASIC 200 houses at least one of the current drivers (i.e. sink or source), a pre-driver stage and a finite-state machine (FSM) based controller 202 among other circuitry. For efficient control, the real-time voltage compensation of the present invention, which is performed during the active charge balance phase, may be implemented within the neurostimulation ASIC 200.

Each of the electrodes 102_0 to 102_N is electrically connected to a dedicated circuitry 204_0 to 204_N within the neurostimulation ASIC 200, called the driver module, which is further supported by a shared common set of circuitry and FSM-based controller 202, as shown in FIG. 2. The controller 202 can also be called an adjustment means 202.

To support stimulation therapy frequencies beyond the tonic frequency range (typically higher than 130 Hz), active charge-balanced stimulation is required to maintain electrical neutrality and safe operation. Though the embodiments of the present disclosure can also be applied with multiphase therapies, a biphasic stimulus pulse is analyzed next as an example, with no loss of generality.

Figure 3:
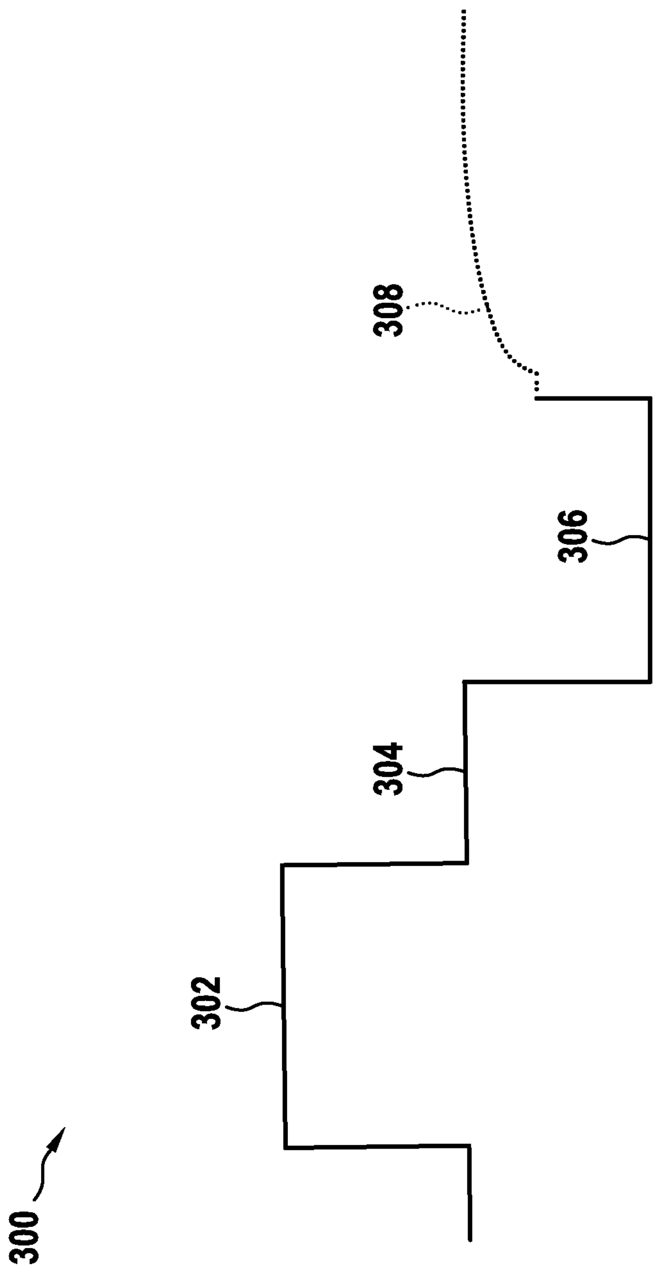
FIG. 3 shows a biphasic pulse with active charge balance.

A biphasic pulse 300 consists of a stimulation phase 302, an interphase period or interphase delay 304 where electrodes electrically float (i.e. are not driven by the IPG), an active charge balance phase 306 and a passive charge balance phase 308, as shown in FIG. 3. The electrodes which deliver stimulation across the tissue are referred to as participating electrodes.

The active charge balance phase 306 employs current which is equal to, or a fraction of, the current in the stimulation phase 302, to revert the charge injected into tissue during the stimulation phase 302. Since this results in a quick discharge, a therapy with a higher pulse rate can be provided. To further ensure electrical neutrality of the electrode-tissue interface and prevent voltage runaway in the DC blocking capacitors, the active charge balance phase 306 may be followed by a passive balance phase 308 where the therapy participating electrodes are electrically shorted together. This also removes any residual charge due to mismatches in the biphasic currents.

According to embodiments of the present disclosure, the voltage accumulated on the capacitive elements of the therapy network during the stimulation phase 302 is negated by a dynamically adjusted programmable voltage drop (or ohmic voltage drop) in the subsequent active charge balance phase 306. At least one dynamically adjustable resistor 206, 208 introduced in series with the active-balance path, being either connected to VISTIM or to VSS, depending on the stimulation configuration, cancels out the accumulated voltage of the stimulation phase 302 in combination with the tissue resistance. Such an arrangement thus compensates for the charge on the capacitive elements, thereby avoiding voltage excursion above or below VISTIM or VSS, respectively.

To implement the above, either an estimated value of the programmable adjustment resistor 206, 208 based on the stimulation pulse feature and stimulation network capacitance is provided or a default value of the programmable adjustment resistor 206, 208 can be used. In either case, the adaptive nature of the real-time ohmic adjustment scheme adjusts the resistor value to be the optimum based on the real-time electrical characteristics of the stimulation network. This dynamic optimization reduces the error in the adjustment of the resistor's values, thus enabling a safe and power-efficient system by cutting down any additional resistive drop and dissipation in the stimulation network.

The real-time ohmic-adjustment scheme, as shown in FIG. 2, is a closed-loop system, wherein the ASIC pads 210_0 to 210_N driving the electrodes 102_0 to 102_N are monitored during therapy and compared with a threshold, which can also be programmable. Each ASIC pad can also be called ASIC driver pad or ASIC current driver pad. The result of this comparison helps the FSM 202 to adjust the programmable adjustment resistor(s) 206, 208. The comparison can be done at the beginning of each active charge balance phase 306 since the resultant voltage is expected to be highest or lowest here, as a result of voltage stacking caused by polarity reversal of undischarged capacitance of the stimulation network.

Non-participating electrodes 102 are the electrodes not involved in the application of therapy but are bio-electrically connected to the participating electrodes through the tissue network. Based on the configuration used for the active charge balancing, one of the participating electrodes as well as few non-participating electrodes are susceptible of experiencing a voltage which is higher than VISTIM or lower than VSS by hundreds of milli-volts (mV). These excursions can cause parasitic diode turn-on resulting in charge-imbalance and current injected into the ASIC 200 substrate. To mitigate this condition, in a preferred embodiment (not shown), a programmable resistor network, realized using an n-bit resistor DAC (digital-to-analog converter), can be introduced in the stimulation network in the active charge balance phase. The resistor DAC combined with the balancing current provides the required ohmic drop to offset the voltage excursions.

As shown in FIG. 2, another preferred embodiment uses two global resistor DACs, namely a first variable resistive element 206 ("RDAC_n") and a second variable resistive element 208 ("RDAC_P"), to support multiple electrodes (e.g. 16 in this example), so this can be scaled, thus making the design area efficient. The first variable resistive element 206 ensures that a voltage on all ASIC 200 pads 210_0 to 210_N driving the electrodes 102_0 to 102_N stay above the lowest voltage rail (VSS) and the second variable resistive element 208 ensures the electrode voltages stay under the highest voltage rail (VISTIM). Each ASIC 200 pad voltage is monitored by monitoring means, such as two dedicated comparators 212 and 214, which can be implemented as strobed comparators to save power. The comparators 212 and 214 feed the FSM 202, which then accordingly updates the corresponding RDAC value to adjust the required ohmic drop.

A preferred embodiment can use MOSFETs (Metal-on-Semiconductor Field Effect Transistors) to realize the programmable DAC to provide ohmic adjustment using drain-to-source on resistance (RDSON) of the MOSFET devices. The DAC may include a programmable binary weighted MOSFET network operated by control signals from the FSM 202. This embodiment can aid in area savings as it avoids the need for large MOSFET switches (low-impedance switches), needed for resistor DAC.

The following sections will provide an overview of possible embodiments of the invention.

Overview of Stimulation and Active Charge Balance

Figure 4A:
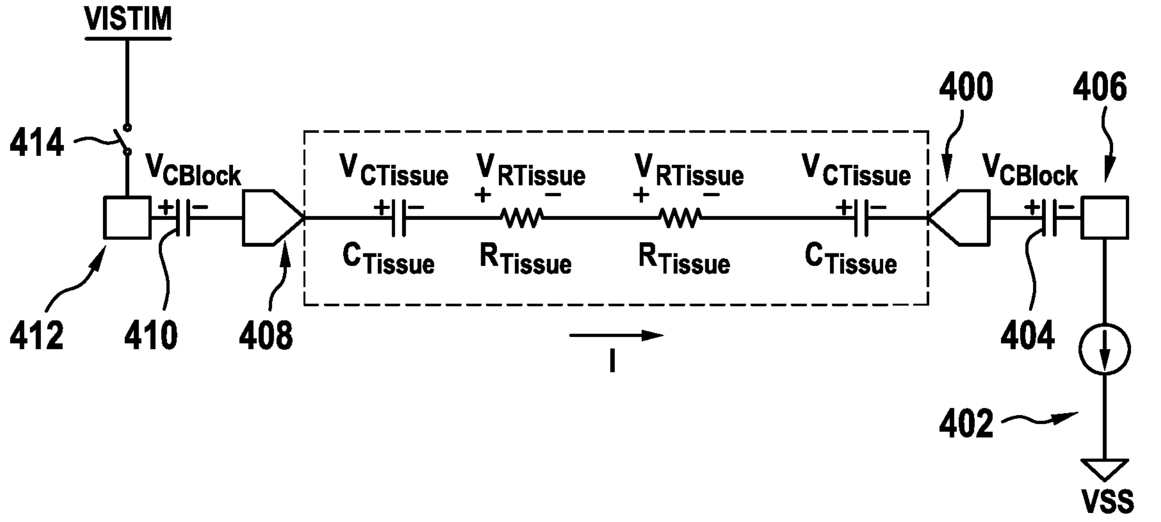
FIGS. 4A and 4B show a current-sink stimulation phase and a current-source active charge balance phase respectively.
Figure 4B:
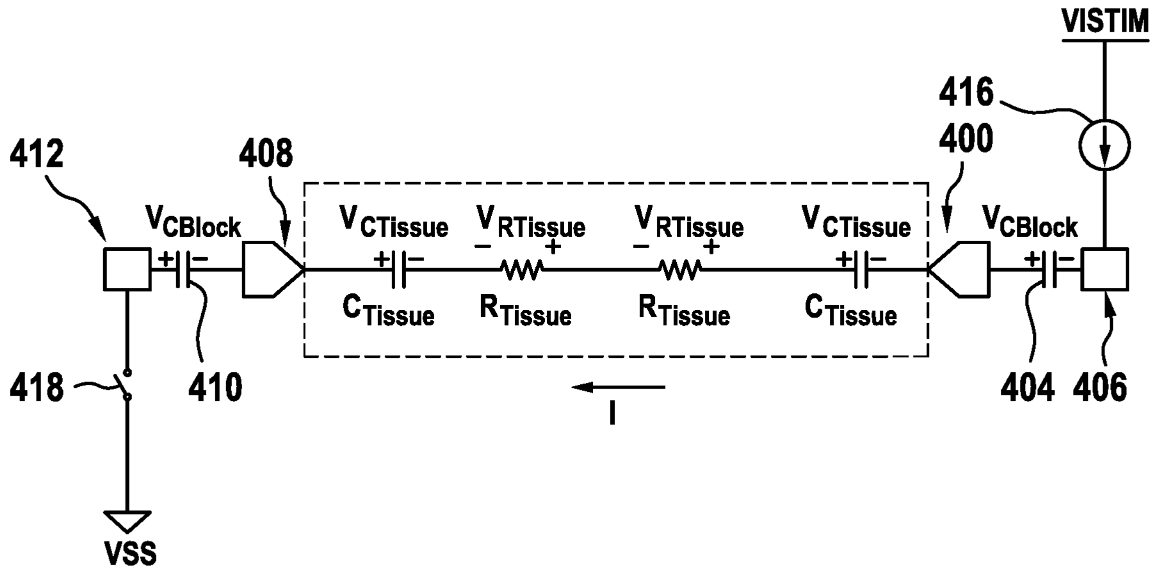

A possible embodiment of delivering stimulation and active charge balancing using two electrodes is shown in FIGS. 4A and 4B. FIG. 4A shows an end of a stimulation phase and FIG. 4B shows a start of an active charge balance phase.

The electrical state at the end of stimulation phase is depicted in FIG. 4A. A stimulation electrode 400 delivers cathodic stimulation to tissue using a current sink 402 to VSS. The stimulation electrode 400 is connected to VSS via a DC-blocking capacitor 404 and a stimulation pad 406. A return electrode 408 completes the electrical path by connecting tissue to the supply rail VISTIM via another DC-blocking capacitor 410, a return pad 412 and an analog switch 414. The stimulation pad 406 and the return pad 412 are ASIC 200 pads.

FIG. 4B shows the start of active charge balance phase. The stimulation electrode 400, in the active charge balance phase, provides the anodic current pulse (current I) using a current source element 416 to maintain charge neutrality across the tissue. This anodic pulse is of opposite polarity relative to the cathodic stimulation pulse.

As the stimulation current pulse imposed by sinking current 402 flows through the stimulation network, the capacitances $C_{TISSUE}$, $C_{BLOCK}$ are polarized and charged, thereby developing a voltage. This voltage can be expressed as in equation 1, where $V_C$ is the voltage across a network capacitor C, $I_{STIM}$ is the stimulation therapy current amplitude, and $T_{PW}$ is the pulse-width of the stimulation pulse.

$$V_C = (I_{STIM} \cdot T_{PW})/C \quad \text{(Eq. 1)}$$

The stimulation current pulse establishes voltage across the tissue capacitors $C_{TISSUE}$ and DC blocking capacitors $C_{BLOCK}$ (equivalent network capacitor C) and this dynamic voltage is highest towards the end of the stimulation phase, as the voltage is directly proportional to time (stimulation pulse-width $T_{PW}$).

Problem Statement—Current-Source Based Active Charge Balance

Applying Kirchhoff's Voltage Law (KVL) to the stimulation network at the end of the stimulation phase (FIG. 4A), the potentials can be expressed as $$V_{RET\_PAD} = V_{CBlock} + V_{CTissue} + V_{RTissue} + V_{RTissue} + V_{CTissue} + V_{CBlock} + V_{STIM\_PAD} \quad \text{(Eq. 2)}$$

where $V_{RET\_PAD}$ is the voltage at the return pad 412 connected to the return electrode 408, $V_{CBlock}$ is the voltage across the DC-Blocking capacitors 404 and 410, $V_{CTissue}$ is the voltage across the double-layer capacitance $C_{TISSUE}$, $V_{RTissue}$ is the voltage across the tissue resistance $R_{TISSUE}$ and $V_{STIM\_PAD}$ is the voltage at the stimulation pad 406 connected to the stimulation electrode 400.

The return pad 412 is connected to VISTIM through a low-impedance connection (analog switch 414), whereas the stimulation pad 406 is a high-impedance node as it is connected to the current sink 402. VRET_PAD and VSTIM_PAD at the end of stimulation phase can be expressed as:

$$V_{RET\_PAD} = VISTIM \quad \text{(Eq. 3)}$$

$$V_{STIM\_PAD} = V_{RET\_PAD} - V_{CBlock} - V_{CTissue} - V_{RTissue} - V_{RTissue} - V_{CTissue} - V_{CBlock} \quad \text{(Eq. 4)}$$

In the active charge balance phase the direction of current reverses and the capacitances in the network maintain the prior voltages and polarities as shown in FIG. 4B.

The return electrode 408 is connected to VSS through a low-impedance connection (analog switch 418), whereas the stimulation electrode 400 is connected to the current source 416 which provides the anodic current pulse. Applying KVL to the stimulation network, the potentials at the beginning of active balance phase (FIG. 4B) can be expressed as:

$$V_{RET\_PAD} = VSS \quad \text{(Eq. 5)}$$

$$V_{STIM\_PAD} = V_{RET\_PAD} - V_{CBlock} - V_{CTissue} - V_{RTissue} - V_{RTissue} - V_{CTissue} - V_{CBlock} \quad \text{(Eq. 6)}$$

Using equation 6, equation 7 can be modified as:

$$V_{STIM\_PAD} = VSS + 2V_{RTissue} - [2V_{CBlock} + 2V_{CTissue}] \quad \text{(Eq. 7)}$$

From equation 7, $V_{STIM\_PAD}$ can have a negative value if the voltage across the stimulation network capacitances is higher than the voltage across the tissue resistance. This implies $V_{STIM\_PAD}$ is susceptible to going below system ground VSS, which is a hazardous condition.

Problem Statement—Current-Sink Based Active Charge Balance

Figure 5A:
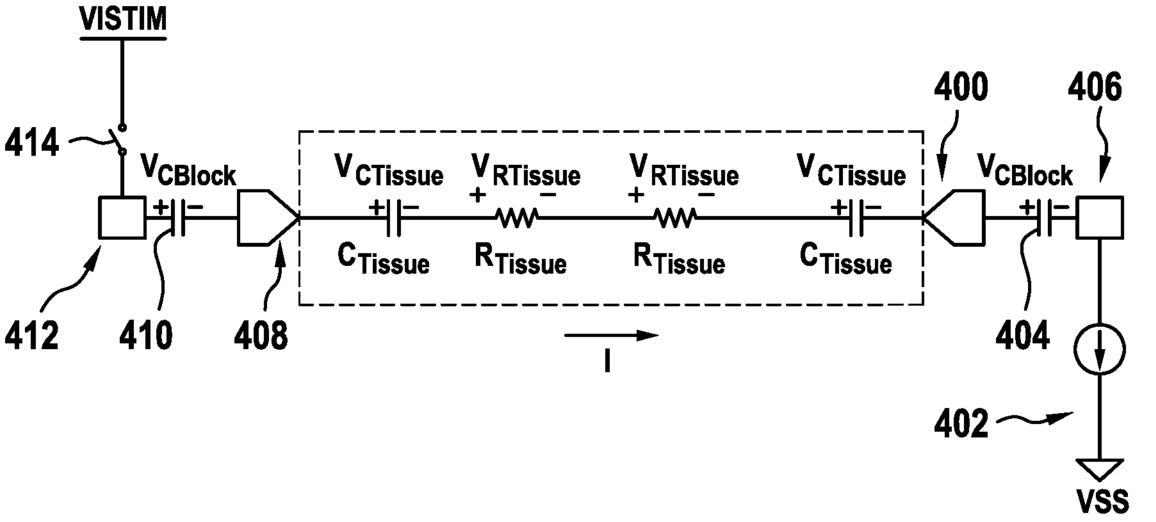
FIGS. 5A and 5B show current-sink-based biphasic stimulation.
Figure 5B:
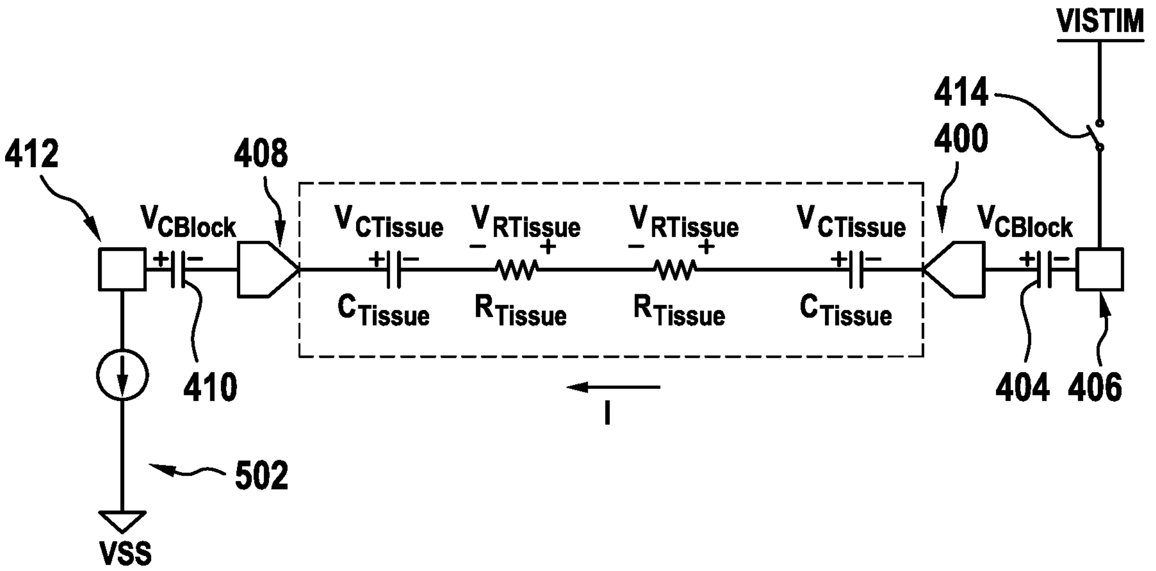

FIGS. 5A and 5B show a current-sink-based biphasic stimulation. FIG. 5A shows an end of a stimulation phase and FIG. 5B shows a start of an active charge balance phase.

A current sink 502 attached to the return electrode 408 is enabled to provide the charge-balancing current. Again, during the active charge balance phase, the current is reversed through the network and the capacitances hold on to the charges and polarity established during the preceding stimulation phase.

The stimulation electrode 400 is connected to VISTIM through a low-impedance connection (analog switch 414), and the return electrode 408 is connected to a current sink 502 which provides the anodic current pulse. Thus, the potential $V_{RET\_PAD}$ at the return pad 412 at the beginning of active balance phase (FIG. 5B) can be expressed as:

$$V_{RET\_PAD} = VISTIM + [2V_{CBlock} + 2V_{CTissue}] - 2V_{RTissue} \quad \text{(Eq. 8)}$$

$V_{RET\_PAD}$ can have a value higher than VISTIM if the voltage across the stimulation network capacitances is higher than the voltage across the tissue resistance. This implies $V_{RET\_PAD}$ is susceptible to going higher than the system supply and activating parasitic diodes.

Problem Solution

From equations 7 and 8, the neurostimulation ASIC 200 pads connected to electrodes 102 participating in the therapy can be at voltage potentials lower than system ground (VSS) and higher than system supply (VISTIM), which can cause charge imbalance and possible electrode damage. This condition can be mitigated by providing a resistor in the stimulation network path only during the active charge balance phase. The proposed scheme, as shown in FIG. 2, provides two resistor DACs, namely the first variable resistive element and the second variable resistive element, such that the resistors can be programmable and can provide for real-time adjustment to protect the neurostimulation system in either of the scenarios.

1. Current-Source-Based Active Charge Balance

Figure 6A:
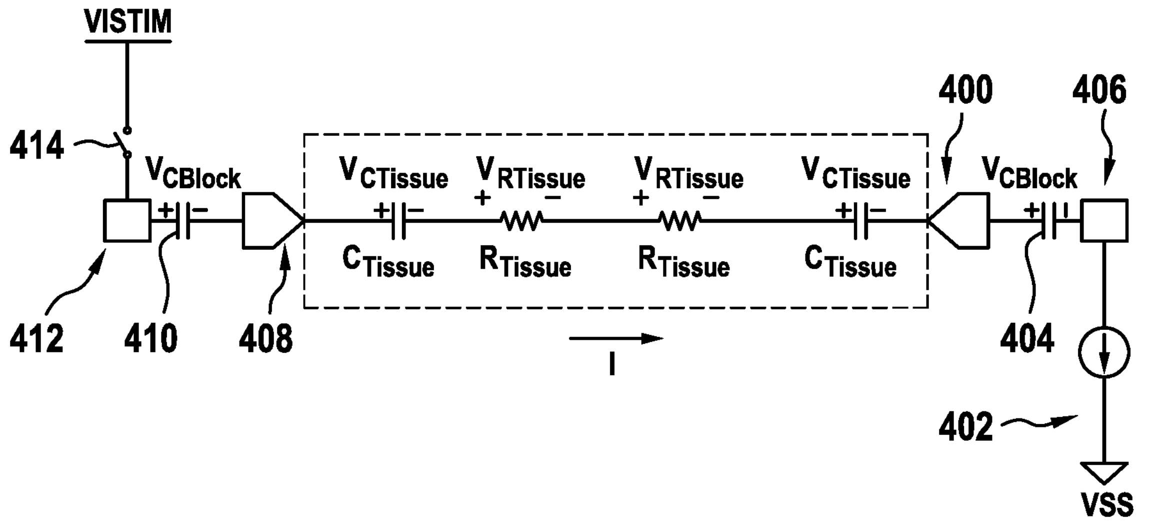
FIGS. 6A and 6B show a current-sink stimulation phase and a current-source-based active charge balance with variable resistance respectively according to embodiments described herein.
Figure 6B:
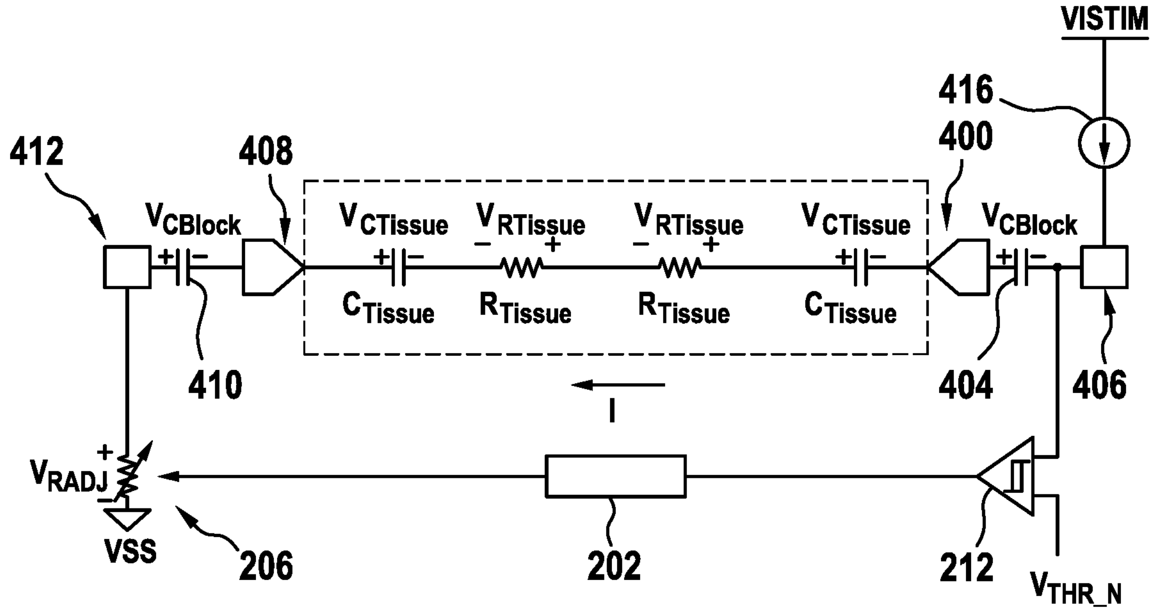

FIGS. 6A and 6B show a current-sink stimulation phase and a current source based active charge balance with variable resistance respectively according to embodiments described herein. FIG. 6A shows an end of a stimulation phase and FIG. 6B shows a start of an active charge balance phase.

To overcome the drawbacks described with respect to FIGS. 4A and 4B, at least one variable resistive element, such as the first variable resistive element 206, can be included in the network during the active charge balance phase. As shown in FIG. 6B, the at least one variable resistive element can be a programmable adjustment resistor ($R_{ADJ}$) which is provided at the return pad 412, which along with the charge balancing current (current I) establishes an voltage (or ohmic voltage) and raises the return pad 412 potential by that ohmic voltage. This results in the return pad 412 to be at a potential higher than the system ground VSS. If this ohmic voltage is maintained such that it offsets the voltage established across the stimulation network capacitances, then the stimulation pad 406 can be prevented from going lower than system ground VSS.

With the at least one variable resistive element 206 in the network, the voltages at the 412, 406 pads are:

$$V_{RET\_PAD} = VSS + V_{RADJ} \quad \text{(Eq. 9)}$$

$$V_{STIM\_PAD} = VSS + V_{RADJ} - V_{CBlock} - V_{CTissue} + V_{RTissue} + V_{RTissue} - V_{CTissue} - V_{CBlock} \quad \text{(Eq. 10)}$$

Equation 10 can be simplified as $$V_{STIM\_PAD} = VSS + V_{RADJ} + 2V_{RTissue} - 2 \cdot [V_{CBlock} + V_{CTissue}] \quad \text{(Eq. 11)}$$

To keep $V_{STIM\_PAD} \geq 0$, the minimum $V_{RADJ}$ can be derived from equation 11 as $$V_{RADJ} \geq 2 \cdot [V_{CBlock} + V_{CTissue}] - 2 \cdot V_{RTissue} \quad \text{(Eq. 12)}$$

Based on equation 12, the minimum adjustment resistance $R_{ADJ}$ can be expressed as $$R_{ADJ} \geq 2 \cdot (T_{PW}/n) \cdot [(C_{BLOCK} + c_{TISSUE})/(C_{BLOCK} \cdot C_{TISSUE})] - 2 \cdot R_{TISSUE} \quad \text{(Eq. 13)}$$

where $T_{PW}$ is the stimulation therapy pulse-width, n is the ratio of stimulation current used as the charge balancing current, and $C_{Block}$, $C_{Tissue}$, and $R_{Tissue}$ have been previously defined.

$R_{ADJ}$ is dependent on the stimulation pulse-width $T_{PW}$, $C_{BLOCK}$, $C_{TISSUE}$, and $R_{TISSUE}$. $T_{PW}$ and $C_{BLOCK}$ are known quantities but $R_{TISSUE}$ and $C_{TISSUE}$ are not and will be variable. The electrode-tissue impedance $C_{TISSUE}$, $R_{TISSUE}$ can be measured and those values can be used, but it entails complexity as well as the measurement will have tolerance. The real-time ohmic adjustment scheme helps in establishing the optimum $R_{ADJ}$ value in either case, thus relaxing additional system complexity and providing safe therapy.

In some cases, $C_{TISSUE}$ can be an assumed value based on available data, thus the combination of $C_{BLOCK}$ and $C_{TISSUE}$ for the entire stimulation network is referred as Effective Capacitance $C_{EFF}$ and used as a starting value for $R_{ADJ}$. For such cases equation 13 can be simplified as $$R_{ADJ} \geq [T_{PW} \cdot C_{EFF}]/n - 2 \cdot R_{TISSUE} \quad \text{(Eq. 14)}$$

2. Current-Sink-Based Active Charge Balance

Figure 7A:
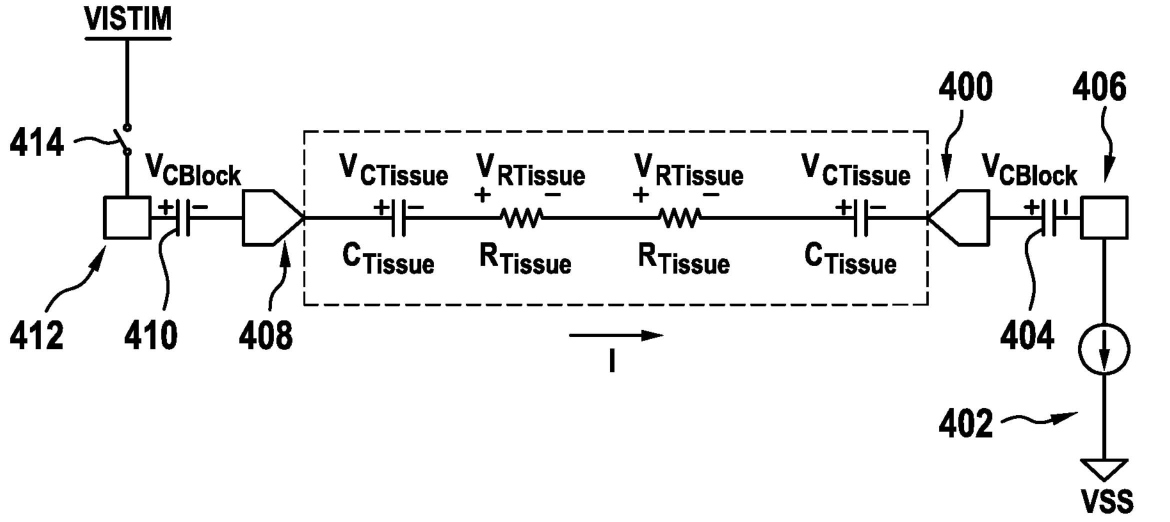
FIGS. 7A and 7B show current-sink-based biphasic stimulation with an active charge balance phase with variable resistance according to embodiments described herein.
Figure 7B:
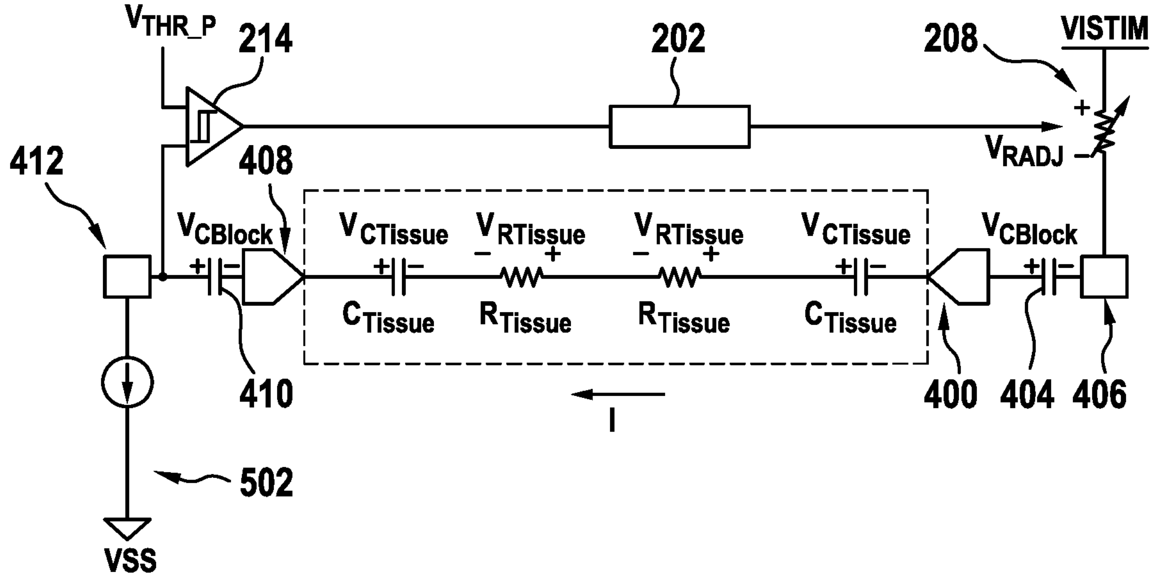

FIGS. 7A and 7B show a current-sink-based biphasic stimulation with and active charge balance phase with variable resistance according to embodiments described herein. FIG. 7A shows an end of a stimulation phase and FIG. 7B shows a start of an active balance phase.

To overcome the drawbacks described with respect to FIGS. 5A and 5B, at least one variable resistive element, such as the second variable resistive element 208, can be included in the network during the active charge balance phase. As shown in FIG. 7B, the at least one variable resistive element can be a programmable adjustment resistor ($R_{ADJ}$) provided at the stimulation pad 406, which along with the charge balancing current (current I) establishes an ohmic drop across the resistor and lowers the stimulation pad 408 potential by that ohmic drop. If this ohmic drop is maintained such that it offsets the voltage established across the stimulation network capacitances, then the return pad 412 can be prevented from going higher than VISTIM. Similarly, it can be shown that the $R_{ADJ}$ required for this configuration is given by the expression in equation 14.

3. Multiple Electrodes

Figure 8A:
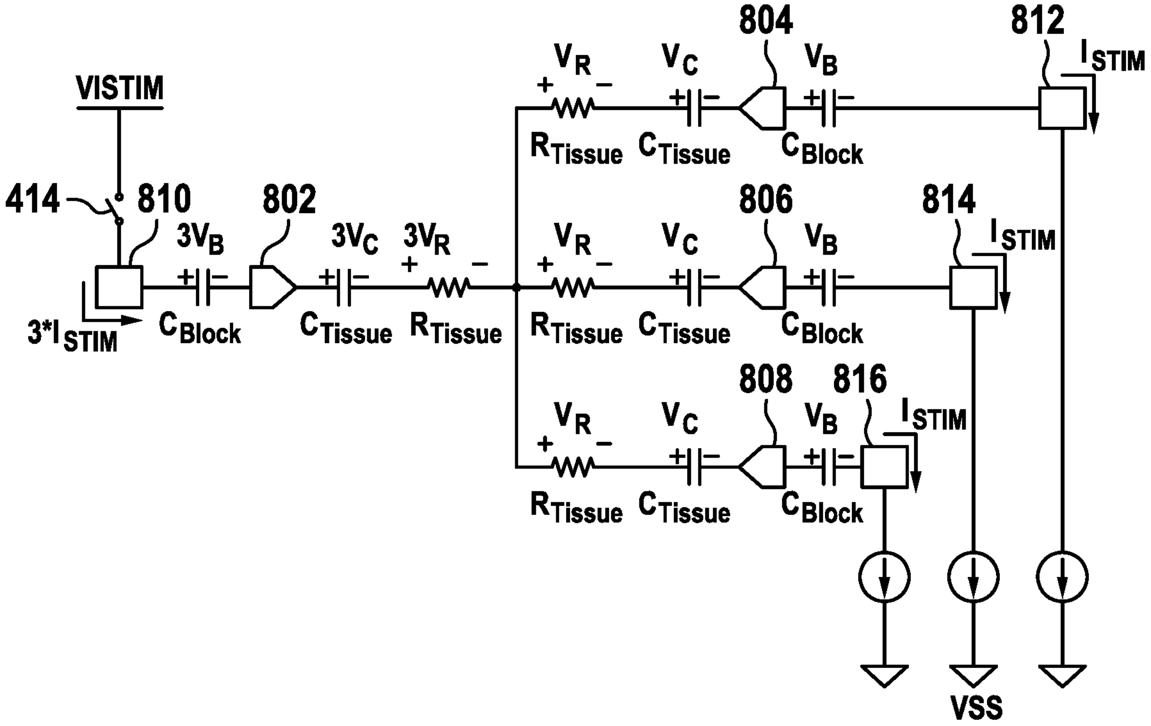
FIGS. 8A and 8B show stimulation and active charge balance phases in a multi-electrode configuration according to embodiments described herein.
Figure 8B:
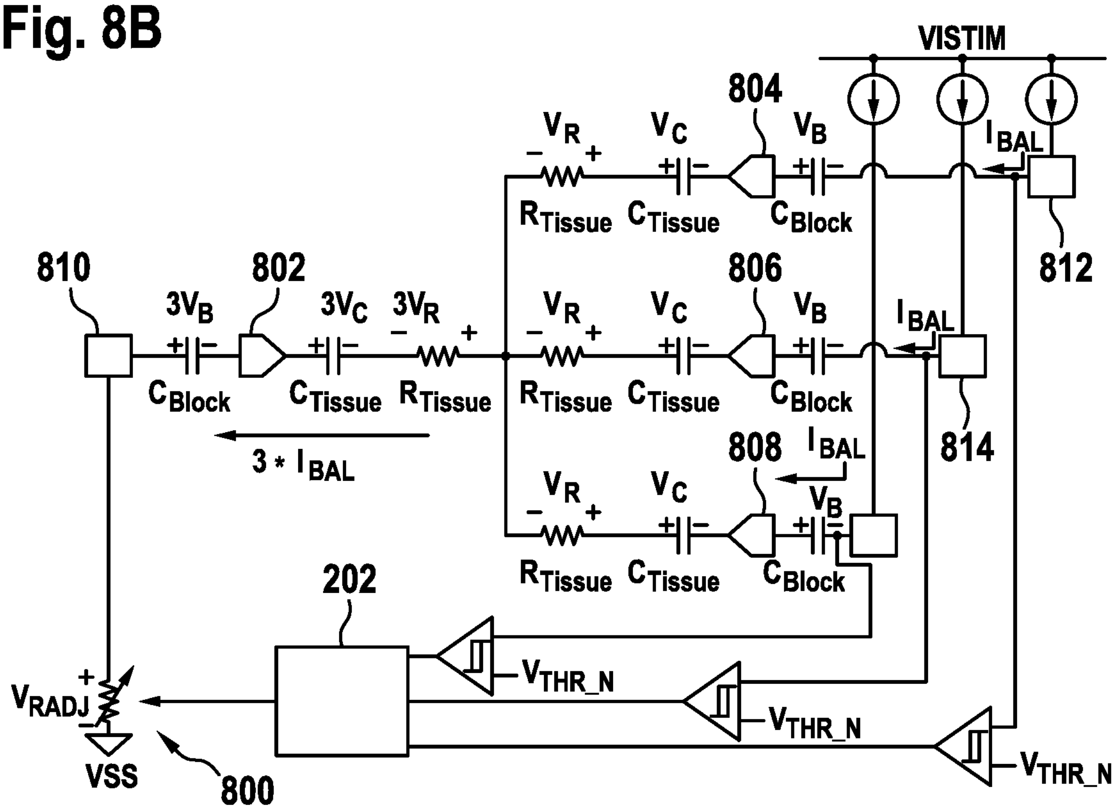

FIGS. 8A and 8B show stimulation and active charge balance phases in a multi-electrode configuration according to embodiments described herein. FIG. 8A shows an end of a stimulation phase and FIG. 8B shows a start of an active charge balance phase.

The scheme explained above is scalable and can be easily applied to scenarios using multiple electrodes (more than two) configured in any combination which is electrically feasible to deliver the intended therapy. Using KVL, specific expressions can be devised to estimate the starting value for the at least one variable resistive element 800 ($R_{ADJ}$). A good estimate of the starting value aids in quicker convergence to the optimum $R_{ADJ}$ value thus enabling a safer and efficient system.

One embodiment of a typical multi-electrode setup is shown in FIGS. 8A and 8B, where cathodic stimulation-based therapy is delivered using three stimulation electrodes 804, 806 and 808 (and corresponding stimulation (driver) pads 812, 814 and 816), and one return electrode 802 (and corresponding return pad 810).

For the setup in FIGS. 8A and 8B, without the at least one variable resistive element 800 in there, all the stimulation (driver) pads 812, 814 and 816 are susceptible to go below the system ground. But with the adjustment resistor 800 instantiated and maintained at the optimum value using the real-time ohmic adjustment scheme, that can be alleviated. Applying KVL to FIG. 8B, during the beginning of the active balance phase, $R_{ADJ}$ can be estimated as $$R_{ADJ} \geq \frac{4}{3} \cdot (T_{PW}/n) \cdot [(C_{BLOCK} + C_{TISSUE})/(C_{BLOCK} \cdot C_{TISSUE})] - \frac{4}{3} \cdot R_{TISSUE} \quad \text{(Eq. 15)}$$

When an effective capacitance ($C_{EFF}$) of the stimulation network is used, equation 15 can be simplified as $$R_{ADJ} \geq \frac{2}{3} \cdot [(T_{PW} \cdot C_{Eff})/n] - \frac{4}{3} \cdot R_{Tissue} \quad \text{(Eq. 16)}$$

In the following, real-time adjustment schemes according to various embodiments of the present disclosure are explained.

Discrete Time Implementation

1. Real-Time Ohmic Adjust Scheme

As $R_{TISSUE}$ and $C_{TISSUE}$ can vary in real-time depending on various physiological factors as well as body posture, the electrical character of the stimulation network becomes dynamic, thus a fixed value of $R_{ADJ}$, which is an estimate, may be insufficient to prevent unwanted excursions. The ohmic adjustment scheme must maintain the value of $R_{ADJ}$ such that excursions at the ASIC driver pads are prevented. To enable this, dedicated ohmic adjustment comparators can be used.

Each driver module may have two comparators—depending on the configuration of therapy delivery used, one of those may observe an excursion and notify the FSM, which then adjusts the corresponding RDAC by a pre-defined value like 1 Lowest Significant Bit (LSB). The LSB decides the resolution and depth of the DAC, so for 8-bit DAC with a LSB of 20Ω, the range of DAC is 5100Ω. Since all the electrodes are connected through the electrolyte, in this case epidural-space tissue, there is an electrical connection between all electrodes in all conditions as shown in FIG. 1, implying susceptibility of non-participating electrodes as well. For robust implementation, this comparator-based monitoring can be extended to all the ASIC driver pads, thus ensuring all the driver pads are within the specified limits of the system supply rails VISTIM, VSS.

In one embodiment, the two comparators 212 and 214 of FIG. 2 are provided at each ASIC driver pad, one for excursion below VSS (the system ground) and one for monitoring the excursion above VISTIM (the system supply) respectively, and can be set to desired thresholds relative to VSS and VISTIM. For ease of implementation and safer operation, a threshold is selected which is under VISTIM and over VSS. In one embodiment of the disclosure, for example, the thresholds can be expressed as equations 17 and 18, where $V_{THR\_P}$ is the threshold for the second comparator 214 and $V_{THR\_N}$ is the threshold for the first comparator 212.

$$V_{THR\_P} = VISTIM - 100\text{ mV} \quad \text{(Eq. 17)}$$

$$V_{THR\_N} = VSS + 100\text{ mV} \quad \text{(Eq. 18)}$$

When an ASIC driver pad 210_0-210_N goes above $V_{THR\_P}$, the second comparator 214 asserts a high and informs the FSM 202 of the excursion. The FSM 202 increases RDAC_P 208, thereby increasing ohmic drop across $R_{ADJ}$, which decreases the driver pad voltage. The adjustment will continue for each stimulation cycle until the second comparator 214 does not assert high, implying the ASIC driver pad is lower than $V_{THR\_P}$=VISTIM−100 mV.

Similarly, when the ASIC driver pad goes below $V_{THR\_N}$, the first comparator 212 asserts a high and informs the FSM 202 of the excursion. RDAC_n 206 is increased, which increases the driver pad voltage. The adjustment will continue until the first comparator 212 does not assert high, implying the ASIC driver pad is higher than $V_{THR\_N}$=VSS+100 mV.

Additionally, when the starting value of $R_{ADJ}$ is higher than the optimum value, implying an over-estimation, the FSM 202 may reduce RDAC_P 208 (or RDAC_n 206) until the comparator 214 (or the comparator 212) detects an excursion. This incremental and decremental adjustment is the adjustment phase of the real-time ohmic adjustment scheme. Since $R_{ADJ}$ can be provided as an estimate using the derivation in equation 14 or may be a system default value, the adjustment phase can take few stimulation therapy cycles depending on the error between the input $R_{ADJ}$ from the optimum real-time $R_{ADJ}$ required by the stimulation network.

Figure 9:
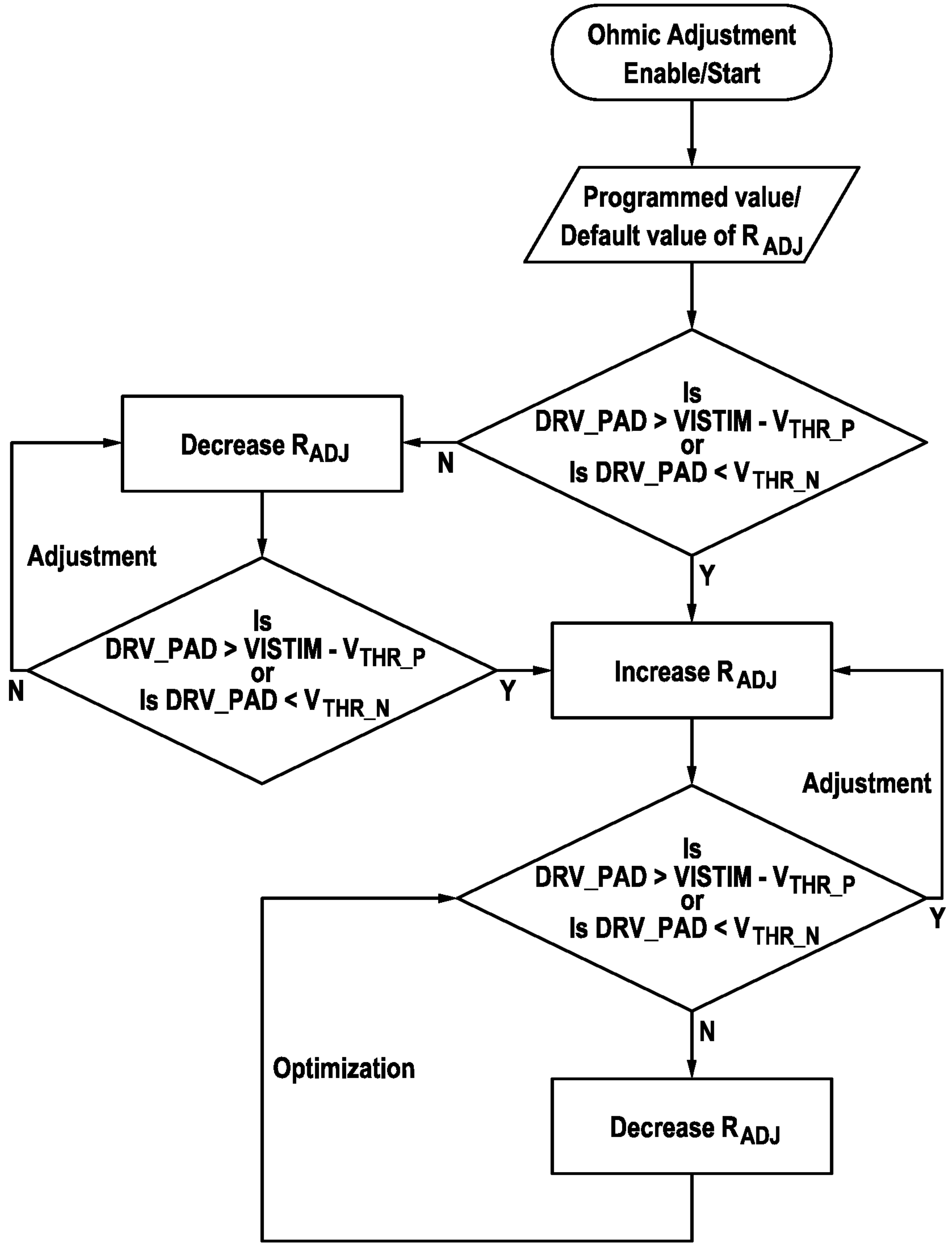
FIG. 9 shows a flowchart of a digitally assisted real-time ohmic adjustment according to embodiments described herein.

The basic functionality of the FSM 202 is summarized in the flow diagram of FIG. 9 discussed in the next section.

2. Real-Time Ohmic Adjust Finite State Machine (FSM)

The stimulation network is an instantaneous electrical network, implying every stimulation cycle the network can present a slightly different electrical character and thus can warrant a different ohmic compensation compared to the prior stimulation cycle. The real-time cycle-by-cycle monitoring of the ASIC driver pads helps the ohmic compensation scheme to be informed and to respond accordingly. The scheme may operate in two phases, as shown in FIG. 9, to provide the appropriate dynamic response based on the instantaneous requirement of the stimulation network to provide safe and power-efficient therapy.

The programmed value/default value of $R_{ADJ}$, if provided, is an estimate, implying it is not the optimum value needed by the system to deliver a power-efficient therapy without any undesired excursions. The real-time ohmic adjustment scheme enforces a balance between safe and efficient therapy using the adjustment phase and optimization phase.

When $R_{ADJ}$ is lower than the optimum value required for a safe, excursion-free stimulation, ohmic adjustment comparators will inform the FSM to increase the value. This increment continues and occurs only if the ohmic adjustment comparators indicate an excursion. Similarly, when the $R_{ADJ}$ value is greater than the optimum value, the ohmic adjustment comparators do not detect any excursion, thereby indicating the FSM to reduce the $R_{ADJ}$ value. The adjustment phase continues until the comparators do not report any excursion or start reporting a $R_{ADJ}$ value greater than the optimum value case. The ohmic adjustment comparators monitor the driver pads every therapy cycle, thus providing the instantaneous feedback regarding the stimulation network's needs.

As $R_{ADJ}$ reaches the value where excursions stop, the ohmic adjustment scheme starts optimizing the $R_{ADJ}$ value by reducing the value of the adjustment resistor DAC. Since the stimulation network is dynamic in nature, without the optimization phase, it is possible that the stimulation system could be operating with an over-estimated $R_{ADJ}$ value and thus a higher system overhead voltage, resulting in a power inefficient therapy. The adjustment phase ensures a safe operation, and the optimization phase delivers a power efficient therapy. Their combination ensures the $R_{ADJ}$ value is very close to the optimum value required by the stimulation network. The ohmic adjustment scheme combines the two phases with dynamic monitoring of the ASIC pads to enable power-efficient and safe neurostimulation therapy using real-time optimized $R_{ADJ}$ values.

When the ASIC driver pad is lower than $V_{THR\_P}$ or higher than $V_{THR\_N}$, it is in a safe operating region and the FSM enters the optimization phase. In this phase, if there are no excursions at the driver pad, implying the outputs of the ohmic adjustment comparators stay low for the next stimulation therapy cycle, then the FSM signals the lowering of RDAC to reduce the $R_{ADJ}$ value. This is effective in the following stimulation therapy cycle. The reduction of the $R_{ADJ}$ value in the optimization phase may or may not trigger a signal from the comparator. If there is a signal, then the ohmic adjustment scheme will enter the adjustment phase and increment $R_{ADJ}$. But if there is no signal from the comparator that implies the $R_{ADJ}$ value was overestimated, the optimization phase continues by reducing $R_{ADJ}$.

3. Real-Time Ohmic Adjust Scheme (Sampled Time)

Figure 10:
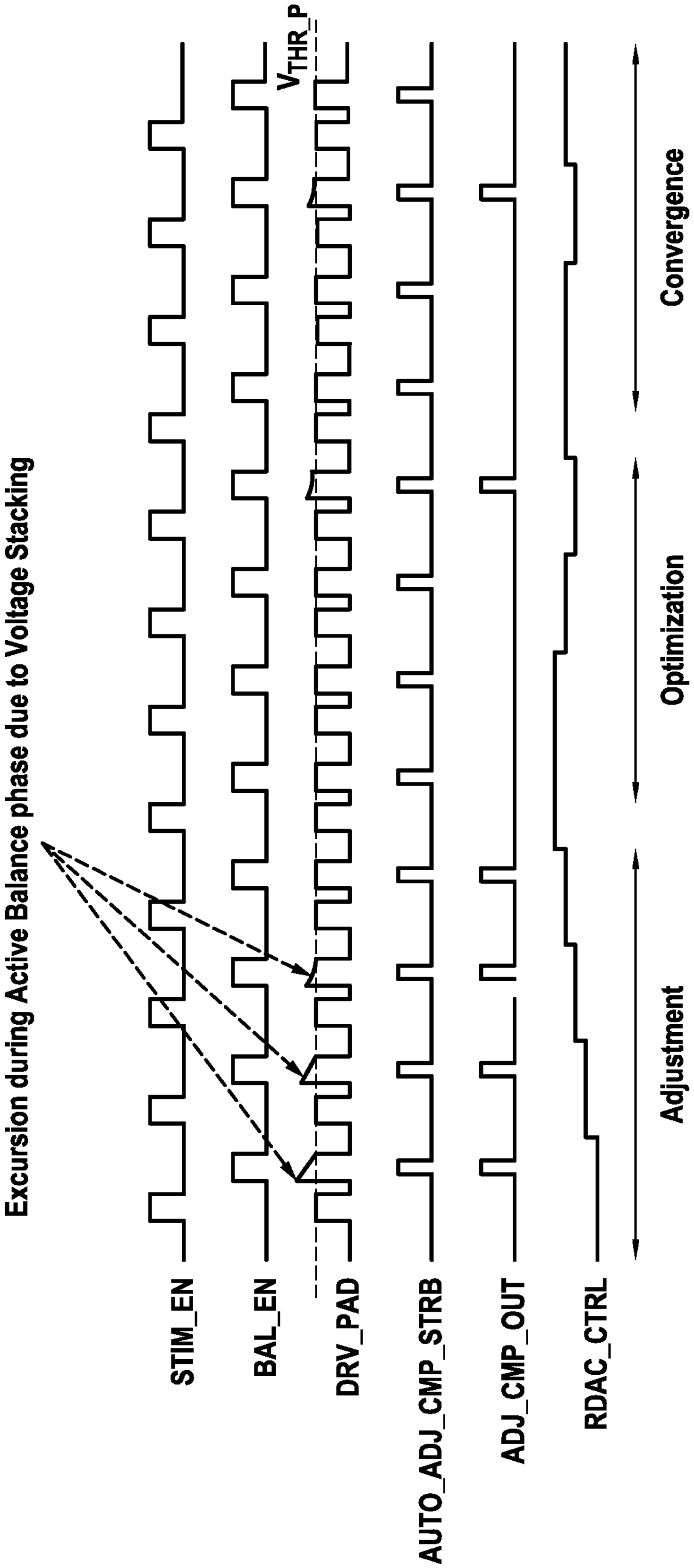
FIG. 10 shows a timing diagram of a digitally assisted real-time ohmic adjustment scheme according to embodiments described herein.

A typical timing diagram of a preferred embodiment of a digitally assisted real-time ohmic adjustment scheme is shown in FIG. 10, and a corresponding possible embodiment of the analog front end was shown in FIG. 2 and is reprinted in FIG. 11 with additional information and signals.

STM_EN and BAL_EN are control signals from FSM 202 which indicate the time when the stimulation phase and active charge balance phase are enabled respectively. The DRV_PAD signal indicates the voltage behavior at one of the ASIC pads 210_0 to 210_N in both the stimulation phase and active charge balance phase, also called active balance phase or active charge phase.

In the active charge balance phase voltage stacking due to charge accumulation on the stimulation network capacitances causes additional voltage to appear at the shown ASIC pad. The additional voltage pushes the voltage at the ASIC pad to cross the ohmic adjustment threshold, $V_{THR\_P}$, as defined in equation 17. This excursion occurs at the beginning of the active balance phase, as the charges on capacitors which were accumulated during the preceding stimulation phase have just started to discharge, as depicted in FIG. 10.

In one embodiment, the ohmic adjustment comparators (212 or 214) can be strobed during this window using the AUTO_ADJ_CMP_STRB signal from the FSM 202, to check for excursions. When the ASIC driver pad goes above $V_{THR\_P}$, the comparator 214 asserts a high and informs the FSM 202 of the excursion. Similarly, when the ASIC driver pad goes below $V_{THR\_N}$, the comparator 212 asserts a high and informs the FSM 202 of the excursion.

The different control signals from the FSM 202 referred to in FIG. 10 and elements of the ASIC 200 which enable the digitally assisted real-time ohmic adjustment scheme are shown in FIG. 11. The RDAC_CTRL signal is the digital code sent to the at least one variable resistive element 206, 208 and in a possible embodiment it is proportional to $R_{ADJ}$.

In the timing diagrams of FIGS. 10 and 12, RDAC_CTRL is assumed to be proportional to $R_{ADJ}$. As shown, whenever there is an excursion, the ADJ_CMP_OUT goes high, implying the $R_{ADJ}$ being used is inadequate and the FSM 202 is informed to increase $R_{ADJ}$. A similar timing diagram can be shown for a condition where the ASIC pads are susceptible to go under $V_{THR\_N}$, as defined in equation 18.

A closer look at the timing diagram example is shown in FIG. 12, where $R_{ADJ}$ is lower than the required optimum adjustment resistor value and the scheme needs four stimulation cycles to stop voltage excursions at the ASIC pad and ensure safe operation. This is the adjustment phase, as shown in FIG. 12(A).

With adequate $R_{ADJ}$ attained, the ohmic adjustment comparator output (either 212 or 214) stays low in a subsequent stimulation cycle and since the comparator output stays low for an additional stimulation cycle, the optimization phase is initiated, as shown in FIG. 12(B). In this phase, the FSM 202 reduces $R_{ADJ}$ to dynamically search for a lower $R_{ADJ}$ value where no excursion is observed. A lower $R_{ADJ}$ value which ensures safe therapy reduces the VISTIM needed to support stimulation, thus enabling a power-efficient stimulation system.

During the optimization phase, if an excursion is observed, then the ohmic adjustment scheme shifts back to the adjustment phase to increase $R_{ADJ}$, as shown by the RDAC_CTRL signal in FIG. 10. The optimization phase not only aids a power-efficient system but also provides a real-time tracking and adjustment of the dynamic stimulation network. The real-time ohmic adjustment scheme uses a combination of an adjustment phase and optimization phase to help RDAC_CTRL converge at a close value to the optimum $R_{ADJ}$ required for providing a safe therapy and power efficient system. This convergence will appear as dithering of the RDAC_CTRL response around the optimum resistance value, as can be seen in FIG. 12(C).

Continuous-Time Implementation

Real-Time Ohmic Adjust Scheme (Continuous Time)

Figure 13A:
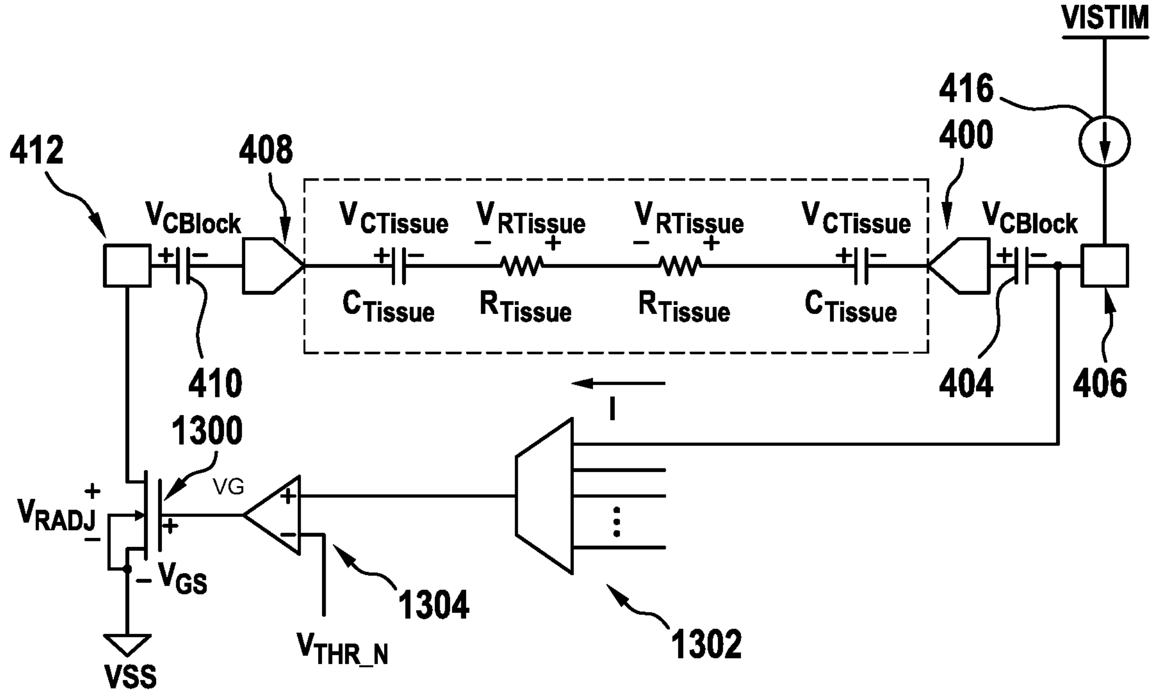
FIG. 13A shows a current-source-based active charge balance with continuous-time feedback according to the embodiments described herein.
Figure 13B:
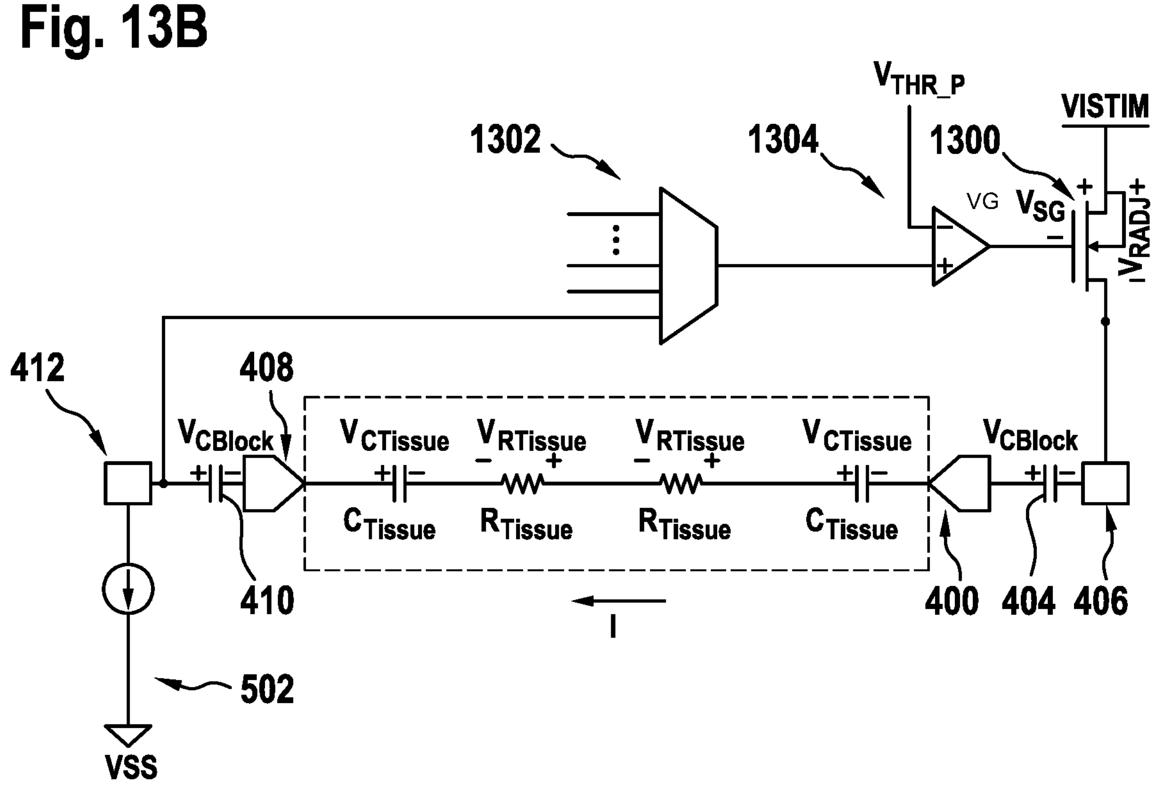
FIG. 13B shows a current-sink-based active charge balance with continuous-time feedback according to embodiments described herein.

In another embodiment shown in FIGS. 13A, 13B and 14, the closed-loop response of the real-time ohmic adjustment scheme can be realized using continuous-time analog feedback where the programmable DAC is replaced by a MOSFET 1300. RDSON of the MOSFET 1300 provides the ohmic adjustment and is controlled by the voltage at the gate terminal, VG. A feedback operational amplifier (op-amp) 1304 sensing the ASIC pad can be used to generate $|V_{GS}|$ such that the ASIC pad is clamped to a desired value, like $V_{THR\_N}$ or $V_{THR\_P}$. Using an analog N:1 selector 1302, the participating ASIC pad is connected to the one input of the feedback op-amp 1304 with the other input at $V_{THR\_N}$ or $V_{THR\_P}$. The selector 1302 provides selectivity as well as enables supporting multi-electrode configurations.

The current-source-based active charge balance phase continuous-time and real-time ohmic adjustment is implemented in the network shown in FIG. 13A. The current-sink-based active charge balance phase continuous-time and real-time ohmic adjustment is implemented in the network shown in FIG. 13B.

This implementation of a closed-loop ohmic adjustment based on continuous-time feedback, shown in FIG. 14, has a much smaller convergence delay and a clamping of the ASIC 200 pad 210_0-210_N is achieved quickly in response to the stimulation network condition. The feedback amplifier 1304 senses the ASIC pad and compares it with the desired threshold voltage $V_{THR\_N}$ (or $V_{THR\_P}$). If the ASIC pad voltage is lower than $V_{THR\_N}$ (or higher than $V_{THR\_P}$) then $V_{GS}$ is decreased (or $V_{SG}$ is decreased) to raise RDSON of the MOSFET 1300. This adjustment happens on-the-fly and is only limited by the feedback loop dynamics. To save power, in one embodiment, the feedback amplifier 1304 can be a strobed amplifier, implying it is enabled only when needed during the active charge balance phase.

When using a pair of MOSFETs (RnMOS and RpMOS) for each ASIC current driver pad 210_0-210_N, large switches can be removed, thereby reducing the size. RnMOS and RpMOS corresponding to the ASIC current driver pads can be selected using a 1: N analog selector and control signals from the FSM 202.

While the foregoing is directed to embodiments of the disclosure, other and further embodiments of the disclosure may be devised without departing from the basic scope thereof, and the scope thereof is determined by the claims that follow.

The invention claimed is:

1. A medical device (100) for electrical stimulation, the medical device (100) comprising:

an electric circuitry configured to perform active charge compensation, the electric circuitry being connectable to at least one electrode arrangement (102) for electrical stimulation, wherein the electric circuitry includes:

(i) monitoring means configured to monitor at least one voltage associated with a stimulation network (108, 116), (ii) at least one variable resistive element (206, 208, 1300) configured to provide a voltage drop used in the active charge compensation, and (iii) adjustment means (202) configured to dynamically adjust a resistance value of the at least one variable resistive element (206, 208, 1300) throughout a duration of the active charge compensation based on the at least monitored voltage, wherein the adjustment means (202) is configured to:

during an adjustment phase, incrementally increase the resistance value when the monitored voltage exceeds a predetermined threshold until no voltage excursion is detected; and during an optimization phase, incrementally decrease the resistance value when no voltage excursion is detected to reduce power consumption while maintaining safe operation.

2. The medical device (100) of claim 1, wherein at least one variable resistive element (206, 208, 1300) is connected in series with an active charge compensation path.

3. The medical device (100) of claim 1, wherein the electric circuitry includes at least one circuitry pad (406, 412) connectable to the at least one electrode arrangement (102), wherein the voltage monitored by the monitoring means is a voltage at the at least one circuitry pad (406, 412).

4. The medical device (100) of claim 3, wherein each electrode arrangement (102) includes a stimulation electrode (400) and a return electrode (408), wherein the at least one circuitry pad (406, 412) includes a stimulation pad (406) connectable to the stimulation electrode (400) and a return pad (412) connectable to the return electrode (408).

5. The medical device (100) of claim 4, wherein the at least one variable resistive element includes a first variable resistor (206, 1300) connected between a system ground (VSS) and the return pad (412), and wherein the monitoring means is configured to monitor a stimulation voltage at the stimulation pad (406) and provide a result of the monitoring to the adjustment means (202).

6. The medical device (100) of claim 5, wherein the adjustment means (202) is configured to adjust the first variable resistor (206, 1300) based on the monitored stimulation voltage to keep a voltage at the stimulation pad (406) above the system ground (VSS).

7. The medical device (100) of claim 4, wherein the at least one variable resistive element includes a second variable resistor (208, 1300) connected between a system voltage (VISTIM) required for the stimulation phase and the stimulation pad (406), and wherein the monitoring means is configured to monitor a return voltage at the return pad (412) and provide a result of the monitoring to the adjustment means (202).

8. The medical device (100) of claim 7, wherein the adjustment means (202) is configured to adjust the second variable resistor (208, 1300) based on the monitored stimulation voltage to keep the voltage at the return pad (412) below the system voltage (VISTIM).

9. The medical device (100) of claim 1, wherein the monitoring means includes at least one comparator (212, 214) configured to compare the monitored voltage to at least one threshold, wherein the at least one comparator (212, 214) is configured to output a result of the comparison to the adjustment means (202).

10. The medical device (100) of claim 1, wherein the at least one variable resistive element (206, 208) is a DAC.

11. The medical device (100) of claim 1, wherein the at least one variable resistive element is a MOSFET (1300), and wherein a drain-to-source on resistance, RDSON, of the MOSFET provides the voltage adjustment.

12. The medical device (100) of claim 1, wherein the electric circuitry is or comprises a neurostimulation programmable application specific integrated circuit (ASIC; 106, 200).

13. A method for active charge compensation in neurostimulation, comprising:

(a) monitoring at least one voltage associated with a stimulation network; and (b) dynamically adjusting a resistance value of at least one variable resistive element throughout a duration of the active charge compensation based on the monitored voltage to provide a voltage drop used in the active charge compensation, wherein dynamically adjusting the resistance value comprises:

(i) during an adjustment phase, incrementally increasing the resistance value when the monitored voltage exceeds a predetermined threshold until no voltage excursion is detected; and (ii) during an optimization phase, incrementally decreasing the resistance value when no voltage excursion is detected to reduce power consumption while maintaining safe operation.

14. A machine-readable medium, comprising instructions executable by one or more processors to implement the method for active charge compensation of claim 13.

15. The method of claim 13, wherein monitoring the at least one voltage comprises:

comparing the monitored voltage to at least one threshold voltage using at least one comparator (212, 214); and providing a result of the comparison to an adjustment means (202) that controls the dynamic adjustment of the resistance value.

16. The method of claim 13, wherein the at least one voltage is monitored at a beginning of an active charge balance phase when voltage stacking from a preceding stimulation phase causes maximum voltage excursion at circuitry pads connected to electrodes.

17. The method of claim 13, wherein dynamically adjusting the resistance value comprises:

monitoring a stimulation pad voltage (VSTIM_PAD) at a stimulation pad (406) connectable to a stimulation electrode (400); and adjusting a first variable resistive element (206, 1300) connected between a system ground (VSS) and a return pad (412) to maintain the stimulation pad voltage above the system ground.

18. The method of claim 13, wherein dynamically adjusting the resistance value comprises:

monitoring a return pad voltage (VRET_PAD) at a return pad (412) connectable to a return electrode (408); and adjusting a second variable resistive element (208, 1300) connected between a system voltage (VISTIM) and a stimulation pad (406) to maintain the return pad voltage below the system voltage.

19. The medical device (100) of claim 10, wherein th is a MOSFET DAC.

20. The method of claim 13, wherein the at least one variable resistive element is a DAC.

* * * * *